United States Patent [19]

Platzek et al.

[11] Patent Number: 5,650,136
[45] Date of Patent: Jul. 22, 1997

[54] CASCADE POLYMER BOUND COMPLEXING COMPOUNDS, THEIR COMPLEXES AND CONJUGATES, PROCESSES FOR THEIR PRODUCTION, AND PHARMACEUTICAL AGENTS CONTAINING THEM

[75] Inventors: Johannes Platzek; Heribert Schmitt-Willich; Heinz Gries; Gabriele Schuhmann-Giampieri; Hubert Vogler; Hanns-Joachim Weinmann; Hans Bauer, all of Berlin, Germany

[73] Assignee: Schering Aktiengesellschaft, Berlin, Germany

[21] Appl. No.: 353,390

[22] Filed: Dec. 2, 1994

Related U.S. Application Data

[60] Continuation of Ser. No. 209,098, Mar. 11, 1994, abandoned, which is a division of Ser. No. 617,077, Nov. 21, 1990, Pat. No. 5,364,614.

[30] Foreign Application Priority Data

Nov. 21, 1989 [DE] Germany ............... 39 38 922.8

[51] Int. Cl.$^6$ .................................. A61B 5/055
[52] U.S. Cl. .......... 424/9.36; 424/9.363; 514/6; 514/54; 514/184; 514/492; 514/836; 436/173
[58] Field of Search ............... 424/9.36, 9.363; 514/6, 54, 184, 492, 836; 556/50, 55, 63, 77, 105, 116, 134, 148; 128/653.4, 654; 436/173; 534/16

[56] References Cited

U.S. PATENT DOCUMENTS

| | | | |
|---|---|---|---|
| 4,071,478 | 1/1978 | Shen et al. | 260/2 R |
| 4,174,428 | 11/1979 | Tabushi et al. | 325/334 |
| 4,587,329 | 5/1986 | Tomalia et al. | 528/363 |
| 4,639,365 | 1/1987 | Sherry | 424/9 |
| 4,647,447 | 3/1987 | Gries et al. | 424/9 |
| 4,885,363 | 12/1989 | Tweedle et al. | 540/465 |
| 4,957,939 | 9/1990 | Gries et al. | 424/9 |
| 4,963,344 | 10/1990 | Gries et al. | 424/9 |
| 4,983,376 | 1/1991 | Sherry | 424/9 |
| 5,087,696 | 2/1992 | Parker et al. | 540/465 |
| 5,136,096 | 8/1992 | Newkome et al. | 564/507 |
| 5,154,853 | 10/1992 | Newkome et al. | 252/311 |
| 5,188,806 | 2/1993 | Sherry et al. | 424/9 |
| 5,198,208 | 3/1993 | Berg et al. | 424/1.1 |
| 5,204,448 | 4/1993 | Subramanian | 530/391.5 |
| 5,338,532 | 8/1994 | Tomalia et al. | 424/1.49 |
| 5,388,532 | 2/1995 | Tomalia et al. | 424/1.49 |

FOREIGN PATENT DOCUMENTS

| | | |
|---|---|---|
| 39794/89 | 2/1993 | Australia. |
| 271180 | 8/1987 | European Pat. Off.. |
| 305320 | 3/1989 | European Pat. Off.. |
| 481526 | 4/1992 | European Pat. Off.. |
| 430863 | 5/1995 | European Pat. Off.. |

OTHER PUBLICATIONS

Tomalia et al., "A New Class of Polymers; . . . ", Polymer Journal, vol. 17, No. 1, pp. 117–132.
Chem. Abstracts 114.123186v, 1991.
Angew. Chem. 103 (1991), Nr. 9, pp. 1205–1207.
Chem. Abstracts 115: 280592n, Dec. 30, 1991.
Chem. Abstracts 115: 256686a, Dec. 16, 1991.
Chem. Abstracts 113: 190723k, 1980.
Chem. Abstracts 115: 257228q, 1991.
Chem. Abstracts 115: 50338e, 1991.

*Primary Examiner*—Gary E. Hollinden
*Attorney, Agent, or Firm*—Millen, White, Zelano, & Branigan, P.C.

[57] ABSTRACT

Cascade polymers, containing complex-forming ligands, optionally at least five ions of an element of atomic numbers 21–29, 39, 42, 44 or 57–83, as well as, if desired, cations of inorganic and/or organic bases, amino acids or amino acid amides, are valuable complexing compounds and complexes for diagnostics and therapy.

14 Claims, 2 Drawing Sheets

CASCADE POLYMER BOUND COMPLEXING COMPOUNDS, THEIR COMPLEXES AND CONJUGATES, PROCESSES FOR THEIR PRODUCTION, AND PHARMACEUTICAL AGENTS CONTAINING THEM

This application is a continuation of application Ser. No. 08/209,098, filed Mar. 11, 1994, now abandoned which is a divisional of application Ser. No. 07/617,077, filed Nov. 21, 1990 U.S. Pat. No. 5,364,614.

BACKGROUND OF THE INVENTION

The invention relates to novel cascade polymer complexing compounds and complexes, agents containing these compounds, the use of the complexes in diagnostics and therapy, as well as processes for the production of these compounds and agents.

"Magnevist" (GdDTPA/dimeglumine) is the first recorded contrast medium for nuclear spin tomography (MRI=magnetic resonance imaging). It is particularly well suited for the diagnosis of pathological areas (e.g., inflammations, tumors, etc.). The compound is eliminated, upon intravenous injection, by way of the kidneys; extrarenal elimination is practically not at all observed.

One disadvantage of "Magnevist" resides in that it is distributed after intravenous administration uniformly between the vasal and interstitial spaces. Accordingly, contrasting of the vessels with respect to the surrounding interstitial space is impossible with the use of "Magnevist".

Especially for the imaging of vessels, a contrast medium would be desirable which is distributed exclusively in the vasal space (vascular space). Such a blood pool agent is to make it possible, with the aid of nuclear spin tomography, to demarcate tissue with good circulation from tissue with poor circulation, and thus to diagnose an ischemia. Also infarcted tissue could be distinguished, on account of its anemia, from surrounding healthy or ischemic tissue with the use of a vasal contrast medium. This is of special importance in case the objective is, for example, to distinguish a cardiac infarction from an ischemia.

Heretofore, most of those patients suspected of harboring a cardiovascular disease (this disease being the most frequent cause of death in Western industrial countries) had to undergo invasive diagnostic tests. In angiography, X-ray diagnostics is presently used, above all, with the aid of iodine-containing contrast media. These tests are burdened by various drawbacks: they bring the risk of radiation stress, as well as discomfort and strain stemming, above all, from the fact that the iodine-containing contrast media must be utilized in a very much higher concentration as compared with NMR contrast media.

Therefore, there is a need for NMR contrast media which can mark the vasal space (blood pool agent). These compounds are to be distinguished by good compatibility and by high efficacy (great increase in signal intensity during MRI).

The premise of solving at least part of these problems by the use of complexing agents bound to macro- or biomolecules has thus far been successful to only a very limited extent.

Thus, for example, the number of paramagnetic centers in the complexes described in European Patent Applications No. 88,695 and No. 150,884 is inadequate for satisfactory imaging.

When increasing the number of required metal ions by repeated introduction of complexing units into a macromolecule, the result is an intolerable impairment of the affinity and/or specificity of this macromolecule [J. Nucl. Med. 24: 1158 (1983)].

Macromolecules are generally suited as contrast media for angiography. Albumin-GdDTPA (Radiology 1987; 162:205), for example, shows, however, an accumulation in liver tissue to an extent of almost 30% of the dose 24 hours after intravenous injection in rats. Besides, only 20% of the dose is eliminated within 24 hours.

The macromolecule polylysine-GdDTPA (European Patent Application, Publication No. 0,233,619) likewise proved to be suitable as a blood pool agent. However, this compound, on account of its production, consists of a mixture of molecules of various sizes. In elimination tests on rats, it could be demonstrated that this macromolecule is eliminated unchanged by glomerular filtration via the kidneys. Due to its synthesis, however, polylysine-GdDTPA can also contain macromolecules which are so large that they cannot pass through the renal capillaries during glomerular filtration and therefore remain in the body.

Macromolecular contrast media based on carbohydrates, for example dextran, have also been described (European Patent Application, Publication No. 0,326,226). The disadvantage of these compounds resides in that they carry normally only 4.6% of the signal-intensifying paramagnetic cation.

SUMMARY OF THE INVENTION

An object, therefore, resides in making available novel diagnostic aids, above all for the recognition and localization of vascular diseases, which aids do not exhibit the aforedescribed disadvantages. This and other objects have been attained by the present invention.

It has been found that complexes comprising nitrogen-containing cascade polymers provided with complexing ligands, ions of an element of atomic numbers 21–29, 39, 42, 44 or 57–83, as well as optionally cations of inorganic and/or organic bases, amino acids or amino acid amides, are surprisingly excellently suitable for the production of NMR and X-ray diagnostic media without exhibiting the aforementioned drawbacks.

The polymers according to this invention can be described by general Formula I

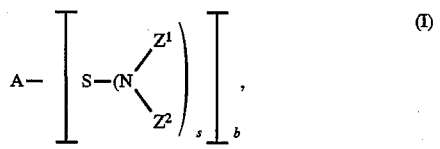

wherein
A means a nitrogen-containing cascade nucleus of basis multiplicity b,
S means a reproduction unit,
N means a nitrogen atom,
$Z^1$ and $Z^2$, for the first to penultimate generation, in each case are

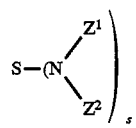

but, for the last generation,
$Z^1$ means a hydrogen atom, a $C_1$–$C_{10}$-alkyl, $C_2$–$C_{10}$-acyl (e.g., alkanoyl) or $C_1$–$C_{10}$-alkylsulfonyl residue, each optionally containing 1–3 carboxy, 1–3 sulfonic acid, 1–5 hydroxy groups and/or 1–3 oxygen atoms (e.g., oxa(—O—) atoms), or it means the residue of a complexing agent or complex K, and $Z^2$ means, to an extent of 96–100%, the residue of a complexing agent or complex K and, to an extent of 4–0%, V' wherein V' is the residue V exhibiting at the end a functional group or, linked via this functional group, a bio- or macromolecule, V meaning a straight-chain, branched, saturated or unsaturated $C_1$–$C_{20}$-alkylene group which optionally contains imino, phenylene, phenylenoxy, phenylenimino, amide, hydrazide, ureido, thioureido, carbonyl, ester group(s), oxygen, sulfur and/or nitrogen atom(s) and is optionally substituted by hydroxy, mercapto, imino, epoxy, oxo, thioxo, and/or amino group(s), b means the numbers 1 through 50, and s means the numbers 1 to 3, wherein the reproduction units S can be different from generation to generation. Also the complex (forming) residues optionally standing for $Z^1$ and $Z^2$ need not be identical. A "generation" is represented by each S group in a chain of S groups.

Examples of alkyl, acyl and alkylsulfonyl residues standing for $Z^1$ that can be cited are:
—$CH_2COOH$; —$(CH_2)_2COOH$; —$CH(COOH)CH_2COOH$; —$CH_2$—$CH(COOH)CH_2OH$; —$CH_2SO_3H$; —$(CH_2)_2SO_3H$; —$COCH_3$; —$COCH_2OH$; —$COCHOHCH_2OH$; —$COCH_2$—$CH_2COOH$; —$CO(CHOH)_4CH_2OH$; —$COCH_2COOH$; —$CO(CH_2)_2COOH$; —$CO(CH_2)_3COOH$; —$CO(CH_2)_4COOH$; —$COCHOHCOOH$; —$CO(CHOH)_2COOH$; —$COCH_2CHOHCH_2COOH$; —$SO_2CH_2COOH$; —$SO_2(CH_2)_2COOH$; —$SO_2CH_3$.

Suitable as the cascade nucleus A are:

$NR^2R^3R^4$, $>N—(CH_2)_a—N—(CH_2)_g—N<$, $>N[(CH_2)_aN]_n—CH_2CH_2—[N(CH_2)_g]_mN<$, $\llcorner[(CH_2)_aN]_k—[(CH_2)_gN]_r\lrcorner$,

[cyclohexane structure with $C_1, C_2, C_3, C_4, C_5$ and W]

[sugar/cyclodextrin structure with $Y^1, Y^2, Y^3$]

wherein $R^2$, $R^3$ and $R^4$ mean, in each case independently of one another, a covalent bond or —$(CH_2)_k$—$(C_6H_4)_r$—$(CH_2)_l$—N< g means the number 2, 3, 4 or 5, t means the number 1, 2, 3, 4, 5, 6, 7 or 8, l means the number 0, 1, 2, 3, 4 or 5, r means the number 0 or 1, n means the number 0, 1, 2, 3 or 4, m means the number 0, 1, 2, 3 or 4, k means the number 1, 2, 3, 4 or 5, a means the number 2, 3, 4 or 5, W means CH, $CH_2$, NH or a nitrogen atom, $C_1$ means $(CH_2)_k$—N<, $C_2$, $C_3$, $C_4$ and $C_5$ mean, in each case independently, a hydrogen atom or $(CH_2)_f$—N<, f means the number 1, 2, 3, 4 or 5, j means the number 6, 7 or 8, $Y^1$ and $Y^2$ mean, in each case independently of each other, a hydrogen atom, $CH_2$—$CH(OH)$—$CH_2N<$ or $(CH_2)_a$—N<, and $Y^3$ is a nitrogen atom, O—$CH_2$—$CH(OH)$—$CH_2N<$ or O—$(CH_2)_g$—N<, a and g are as defined above, --- means a single or double bond, with the proviso that, if $Y^3$ is a nitrogen atom, $Y^1$ and $Y^2$ mean hydrogen. $C_6H_4$ is phenylene.

The simplest case of a cascade nucleus is represented by the nitrogen atom, the three bonds of which (basis multiplicity b=3) are occupied in a first "inner layer" (generation 1) by three reproduction units S each of which carries 1 to 3 terminal $NH_2$ groups (s=1–3) (or, alternatively, the three hydrogen atoms of the basic cascade starter ammonia have been substituted by three units S). If the reproduction unit S contains, for example, an $NH_2$ group (s=1), then the reproduction multiplicity of this generation is 2 s=2. The second layer (generation 2) of reproduction units S introduced in a subsequent reaction sequence (occupying, in the above-mentioned example with A=nitrogen atom and s=1, six bonds) need not be identical with the reproduction units S of the first generation. After preferably maximally 10, most preferably 2–6 generations, the terminal nitrogen atoms of the outermost layer are substituted as indicated above for $Z^1$ and $Z^2$ of the final generation.

Further preferred cascade starters $A(H)_b$ that can be listed are, inter alia:

tris(aminoethyl)amine (b=6);
tris(aminopropyl)amine (b=6);
diethylenetriamine (b=5);
triethylenetetramine (b=6);
tetraethylenepentamine (b=7);
$H_2N$—$CH_2$—$C_6H_4$—$CH_2$—$NH$—$CH_2$—$C_6H_4$—$NH_2$ (b=5);
1,3,5-tris(aminomethyl)benzene (b=6);
2,4,6-tris(aminomethyl)pyridine (b=6);
1,4,7-triazacyclononane (b=3);
1,4,7,10-tetraazacyclododecane (b=4);
1,4,7,10,13-pentaazacyclopentadecane (b=5);
1,4,8,11-tetraazacyclotetradecane (b=4);
1,4,7,10,13,16,19,22,25,28-decaazacyclotriacontane (b=10);
6,6',6'',6''',6'''',6'''''-hexaamino-6,6',6'',6'''-6'''',6'''''-hexadeoxy-α-cyclodextrin (b=12);
6,6',6'',6''',6'''',6''''',6''''''-heptaamino-6,6',6'',6''',6'''',6''''', 6''''''-heptadeoxy-β-cyclodextrin (b=14);
6,6',6'',6''',6'''',6'''''-hexa-(1-amino-2-hydroxy-propyl)-α-cyclodextrin hexaether (b=12);
2,2',2'',2''',2'''',2''''',6,6',6'',6''',6'''',6'''''-dodeca-(1-amino-2-hydroxypropyl)-α-cyclodextrin dodecaether (b=24).

Thus, b generally is the number of cascadable (reacting) nitrogen valences (bonds) in an A group, e.g., corresponding to the number of H atoms bonded to N atoms.

The reproduction unit S typically has the formula $$-(CH_2)_2-CONH-(CH_2)_a-$$

or $$-CH_2-CH(OH)-(CH_2)_k-(O)_r-(CH_2)_l-C\underset{\gamma}{\overset{\alpha}{\underset{\beta}{<}}}$$

wherein
a is a number 2, 3, 4 or 5,
α and β in each case mean a hydrogen atom or $(CH_2)_o$,
γ means $(CH_2)_f$,
k is 1, 2, 3, 4 or 5,
l is 0, 1, 2, 3, 4 or 5,
o is 0, 1, 2, 3, 4 or 5,
f means the number 1, 2, 3, 4 or 5, and
r means the number 0 or 1, with the proviso that o and l are not both zero at the same time, Preferred reproduction units S are $$-(CH_2)_2-CONH-(CH_2)_2-;$$

$$-CH_2-CH(OH)-CH_2-;$$

$$-CH_2-CH(OH)-CH_2-O-(CH_2)_2-;$$

$$-CH_2-CH(OH)-CH_2-O-CH\underset{CH_2-}{\overset{CH_2-}{<}};$$

$$-CH_2-CH(OH)-CH_2-O-CH_2-CH\underset{CH_2-}{\overset{CH_2-}{<}};$$

$$-CH_2-CH(OH)-CH_2-O-CH_2-C\underset{CH_2-}{\overset{CH_2-}{\underset{|}{-}}}CH_2-.$$

Suitable complex (forming) residues K are described by general Formulae I A, I B and I C:

$$\begin{array}{c}CH_2CO-\\|\\N-(CH_2-CH_2-N)_n-CH_2-CH_2-(N-CH_2-CH_2)_m-N\\|\quad\quad\quad\quad\quad\quad\quad\quad\quad|\quad\quad\quad\quad\quad\quad\quad\quad\quad\quad\quad|\\CH_2X\quad\quad\quad CH_2X\quad\quad CH_2X\quad\quad\quad\quad CH_2X\end{array}\quad (I\,A)$$

$$\begin{array}{c}U\quad\quad\quad R^1\quad\quad CH_2X\\|\quad\quad\quad\quad|\quad\quad\quad\;\;|\\N-(CH_2)_k-CH-(CH_2)_l-N\\|\quad\quad\quad\quad\quad\quad\quad\quad\quad\quad\quad|\\B\quad\quad\quad\quad\quad\quad\quad\quad\quad D\\|\quad\quad\quad\quad\quad\quad\quad\quad\quad\quad|\\N\underline{\quad\quad\quad\quad\quad\quad}(E-N)_q\\|\quad\quad\quad\quad\quad\quad\quad\quad\quad\quad|\\CH_2X\quad\quad\quad\quad\;\;CH_2X\end{array}\quad (I\,B)$$

(I C) pyridine-type structure with R¹ at top, U–N and N–U groups at the 2,6-positions connected via a macrocycle containing N–U.

wherein n and m in each case independently mean the number 0, 1, 2, 3 or 4, n and m adding up to no more than 4,
k means the number 1, 2, 3, 4 or 5,
l means the number 0, 1, 2, 3, 4 or 5,
q means the number 0, 1 or 2,
U is $CH_2X$ or V,
X means in each case independently the residue —COOH or V' wherein, if the molecule contains V', at least 0.1% of the substituents X stand for V',
B, D and E, being identical or different, mean in each case the group $-(CH_2)_a$ with a meaning the number 2, 3, 4 or 5,
$R^1$ means V or a hydrogen atom,
V and V' are as defined above, with the proviso that $R^1$ means V only if U means $CH_2X$ at the same time, and that U means V only if $R^1$ means a hydrogen atom at the same time, as well as with the proviso that, if desired, a portion of the COOH groups is present as ester and/or amide.

Examples that can be cited for the complex forming residues K are those of ethylenediaminetetraacetic acid, diethylenetriaminepentaacetic acid, trans-1,2-cyclohexanediaminetetra-acetic acid, 1,4,7,10-tetraazacyclododecanetetraacetic acid, 1,4,7-triazacyclononanetriacetic acid, 1,4,8,11-tetraazatetradecanetetraacetic acid, 1,5,9-triazacyclododecanetriacetic acid, 1,4,7,10-tetraazacyclododecanetriacetic acid and 3,6,9,15-tetraazabicyclo[9.3.1]pentadeca-1(15),11,13-trienetriacetic acid which are linked via (in each case contained in K) a carbonyl group (I A; I B and I C, contained in V, e.g., where U is V if $R^1$ means a hydrogen atom at the same time) or via a carbon atom (contained in V, see definition for U and $R^1$ as per above, e.g., in I B and I C where $R^1$ is V if U stands for $CH_2X$ at the same time) to respectively one terminal —$NH_2$ group of the final generation of the cascade polymer. If desired, a portion of the carboxylic acids can be present as converted to ester and/or amide groups.

As $Z^2$ of the last generation, V' can also be present up to a proportion of 4%.

Suitable complexes for $Z^1$ and $Z^2$ correspond to the foregoing complexing (chelating) agents as bonded (chelated) to central metal ions.

If the medium of this invention is intended for use in NMR diagnostics, then the central ion of the complex salt must be paramagnetic. These are, in particular, the di- and trivalent ions of the elements of atomic numbers 21–29, 42, 44 and 58–70. Suitable ions are, for example, the chromium (III), manganese(II), iron(II), cobalt(II), nickel(II), copper (II), praseodymium(III), neodymium(III), samarium(III) and ytterbium(III) ions. On account of their very strong magnetic moment, gadolinium(III), terbium(III), dysprosium (III), holmium(III), erbium(III) and iron(III) ions are especially preferred.

In case the agent of this invention is meant for use in X-ray diagnostics, the central ion must be derived from an element of a higher atomic number in order to obtain adequate absorption of the X rays. It has been found that diagnostic aids are suitable for this purpose which contain a physiologically compatible complex salt with central ions of elements of atomic numbers between 21–29, 39, 42, 44, 57–83; these are, for example, the lanthanum(III) ion and the above-mentioned ions of the lanthanide series.

The cascade polymer complexes according to this invention contain at least five of the ions of an element of the aforementioned atomic numbers.

The alkylene group standing for V as well as the hydrocarbyl group standing for R and R' (below) can be straight-chain, branched, cyclic, aliphatic, aromatic or arylaliphatic and can contain up to 20 carbon atoms. Straight-chain monoto decamethylene groups as well as $C_1$–$C_4$-alkylenephenyl groups are preferred. The following alkylene groups are cited as examples for explanatory purposes:

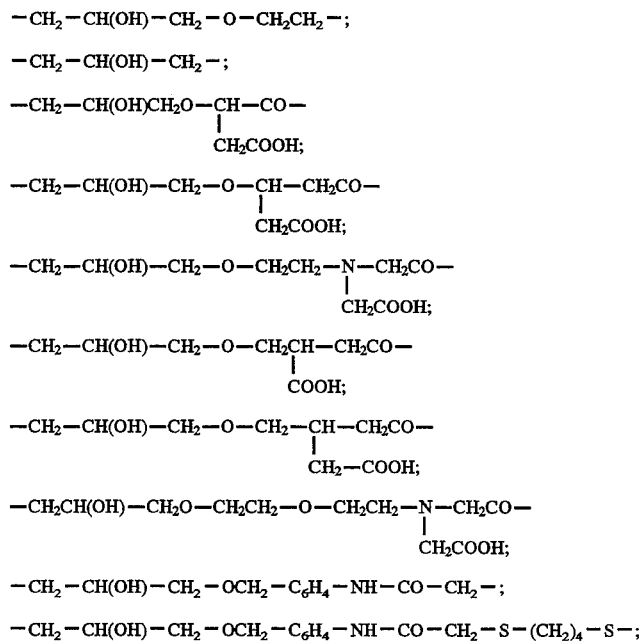

wherein $R^+$ and $R^y$ stand for natural amino acid residues;
—$CH_2$—$CH(OH)$—$CH_2$—$O$—$(CH_2)_2$—$NHCS$—;
—$CH_2$—$CH(OH)$—$CH_2$—$NHCS$—; —$CH_2$—$CH(OH)$—$CH_2$—$O$—$(CH_2)_2$—$O$—$(CH_2)_2NHCS$—; —$CH_2$—$CH(OH)$—$CH_2$—$O$—$(CH_2)_2$—$NH$—$CO$—$CH_2$—; —$CH_2$—$CH(OH)$—$CH_2$—$O$—$C_6H_4$—$NHCS$—; —$CH_2$—$CH(OH)$—$CH_2$—$O$—$C_6H_4$-$NHCO$—; —$CH_2$—$CH(OH)$—$CH_2$—$O$—$CH_2$—$C_6H_4$—$NHCS$—; —$CH_2$—$O$—$C_6H_4$—$CH_2$—; —$CH_2$—$CH(OH)$—$CH_2$—$O$—$C_6H_4$—$CH_2$—; —$C(=NH)$—$O$—$C_6H_4$——$CH_2$—; —$(CH_2)_4$—$NH$—$CO$—$CH_2$—$O$—$C_6H_4$—$CH_2$—; —$(CH_2)_4$—$NH$—$CH_2$—$CH(OH)$—$CH_2$—$O$—$C_6H_4$—$CH_2$—; —$(CH_2)_3$—$O$—$C_6H_4$—$CH_2$—; —$CH_2$—$CO$—$NH$—$(CH_2)$—$O$—$CH_2$—; —$CH_2$—$CO$—$NH$—$NH$—; —$CH_2$—$CONH$—$(CH_2)_2$; —$CH_2$—$CO$—$NH$—$(CH_2)_{10}$—; —$CH_2$—$CONH$—$(CH_2)_2$—$S$—; —$(CH_2)_4$—$NH$—$CO$—$(CH_2)_8$—; —$CH_2$—$CO$—$NH$—$(CH_2)_3$—$NH$—; —$(CH_2)_3$—$NH$— groups.

Preferred functional groups located at the end of the V" alkylene group are, for example, the maleimidobenzoyl, 3-sulfomaleimidobenzoyl, 4-(maleimidomethyl)cyclohexylcarbonyl, 4-[3-sulfo-(maleimidomethyl)cyclohexyl]carbonyl, 4-(p-maleimidophenyl)butyryl, 3-(2-pyridyldithio)propionyl, methacryloyl(pentamethylene) amido, bromoacetyl, iodoacetyl, 3-iodopropyl, 2-bromoethyl, 3-mercaptopropyl, 2-mercaptoethyl, phenyleneisothiocyanate, 3-aminopropyl, benzyl ester, ethyl ester, tert-butyl ester, amino, $C_1$–$C_6$-alkylamino, aminocarbonyl, hydrazino, hydrazinocarbonyl, maleimido, methacrylamido, methacryloylhydrazinocarbonyl, maleimidamidocarbonyl, halogeno, mercapto, hydrazinotrimethylenehydrazinocarbonyl, aminodimethyleneamidocarbonyl, bromocarbonyl, phenylenediazonium, isothiocyanate, semicarbazide, thiosemicarbazide, isocyanate groups. Several selected groups will be set forth for explanatory purposes:

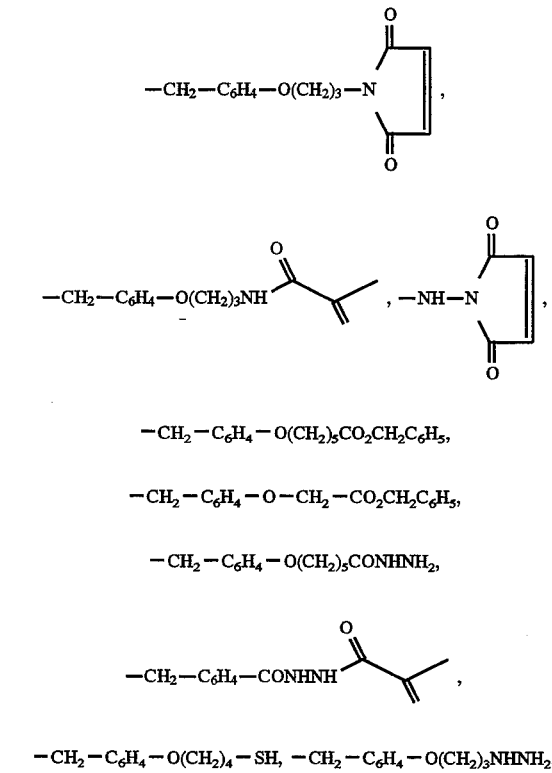

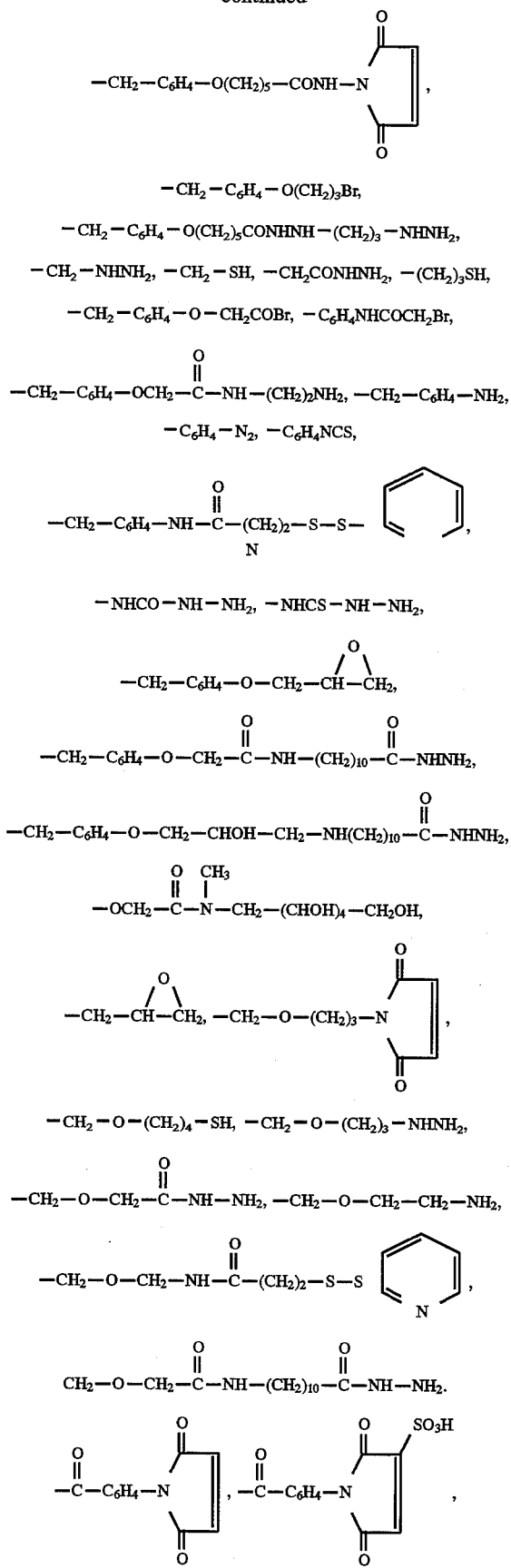

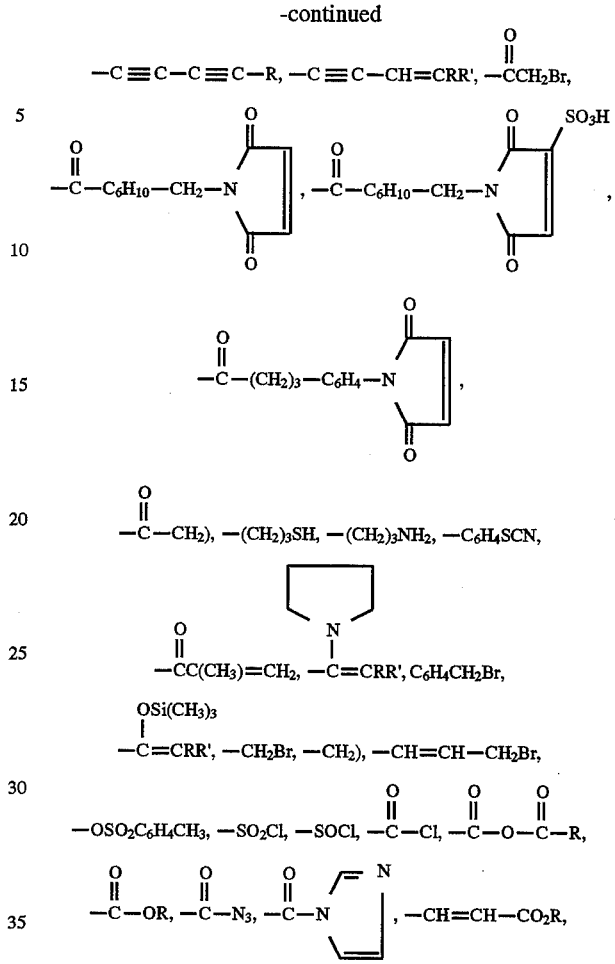

wherein R and R' are identical or different and mean in each case a hydrogen atom, a saturated or unsaturated $C_1$–$C_{20}$-hydrocarbyl residue optionally substituted by a phenyl group, or a phenyl group.

The residual acidic hydrogen atoms, i.e. those that have not been substituted by the central ion, can be replaced, if desired, entirely or partially by cations of inorganic and/or organic bases or amino acids. The corresponding acid groups can also be converted entirely or partially into esters or amides.

Suitable inorganic cations are, for example, the lithium ion, the potassium ion, the calcium ion, the magnesium ion, and especially the sodium ion. Suitable cations of organic bases are, inter alia, those of primary, secondary or tertiary amines, e.g. ethanolamine, diethanolamine, morpholine, glucamine, N,N-dimethylglucamine and, in particular, N-methylglucamine. Suitable cations of amino acids are, for example, those of lysine, of arginine and of ornithine, as well as the amides of otherwise acidic or neutral amino acids.

Suitable esters are preferably those with a $C_1$–$C_6$-alkyl residue; examples that can be cited are the methyl, ethyl and tert-butyl residues.

In case the carboxylic acid groups are to be present at least in part as amides, then tertiary amides are preferred. Suitable residues are saturated, unsaturated, straight- or branched-chain or cyclic hydrocarbons of up to 5 carbon atoms optionally substituted by 1–3 hydroxy or $C_1$–$C_4$-alkoxy groups. Examples that can be cited are the methyl, ethyl, 2-hydroxyethyl, 2-hydroxy-1-(hydroxymethyl)ethyl, 1-(hydroxymethyl)ethyl, propyl, isopropenyl, 2-hydroxypropyl, 3-hydroxypropyl, 2,3-dihydroxypropyl, butyl, isobutyl, isobutenyl, 2-hydroxybutyl, 3-hydroxybutyl, 4-hydroxybutyl, 2-, 3- and 4-hydroxy-2-methylbutyl, 2- and 3-hydroxyisobutyl, 2,3,4-trihydroxybutyl, 1,2,4-trihydroxybutyl, pentyl, cyclopentyl and 2-methoxyethyl groups. The amide residue can also be a heterocyclic 5- or 6-membered ring formed with inclusion of the amide nitrogen. Examples in this connection are: the pyrrolidinyl, piperidyl, pyrazolidinyl, pyrrolinyl, pyrazolinyl, piperazinyl, morpholinyl, imidazolidinyl, oxazolidinyl, thiazolidinyl rings.

The compounds of this invention exhibit the desirable properties set forth hereinabove. They contain the large number of metal ions, required for their use, bound in the complex in a stable fashion. They are distributed (if V' does not contain a bio- or macromolecule) only in the vasal space and thus can map this space with the aid of nuclear spin tomography.

The compatibility of the compounds according to this invention is improved by at least a factor of 3 over "Magnevist" ($LD_{50}$ i.v. mice of Example 8: 30 mmol/kg; "Magnevist":≦10).

The value of osmolality, responsible for side effects, such as pain, damage to the blood vessels and cardiovascular disturbances, is reduced as compared with "Magnevist" (Example 8: 0.46 [osmol/kg] as compared with "Magnevist" 1.96 [osmol/kg], 0.5 mol/l at 37° C.).

The value for the magnitude of relaxation, representing a measure for imaging in MRI, is surprisingly high; signal intensification could be increased over "Magnevist", for example in case of the compound of Example 8, fourfold.

As compared with the macromolecular contrast media based on carbohydrates, e.g. dextran (European Patent Application, Publication No. 0,326,226) which carry—as mentioned—normally only 4.6% of the signal-intensifying paramagnetic cation, the polymer complexes of this invention contain more than 15% of the paramagnetic cation. Accordingly, the macromolecules of this invention bring about, per molecule, a very much higher signal intensification which has the result, at the same time, that the dose required for nuclear spin tomography is considerably smaller as compared with that for macromolecular contrast media based on carbohydrates.

It has been made possible with the polymer complexes according to this invention to construct and produce macromolecules in such a way that they exhibit a uniformly defined molecular weight. Such macromolecular contrast media, exactly definable in their molecular size, have not been accessible heretofore. It is thus surprisingly possible for the first time to regulate the size of the macromolecules so that these are large enough to be able to leave the vasal space only gradually but, at the same time, small enough to still pass through the kidney capillaries which have a size of 300–800 Å. It has thus been accomplished for the first time to produce macromolecular contrast media tailored to the body.

The complexes of this invention serve as contrast media for imaging the vessels by means of nuclear spin tomography. It is thus possible to differentiate between ischemic tissue and normal tissue. However, also other damage to the blood-tissue barrier can be recognized by means of these compounds. In case of inflammations and tumors in the brain, the blood-brain barrier is damaged to such an extent that the contrast medium can infiltrate the diseased tissue and thus the diseased tissue becomes visible in nuclear spin tomography. On account of the impermeability of the intact blood-brain barrier, even to small, but hydrophilic molecules, inflammations and tumors have also been recognizable even with the low-molecular compound "Magnevist". However, when using the complexes of this invention in these cases, the dosage can be reduced sixteenfold, for two reasons: (1) they exhibit a signal intensification which is four times higher, and (2) they are distributed in a space that is four times smaller, namely only in the vasal space, i.e. in order to reach the same concentrations in the blood, one-fourth of the dose is sufficient.

Another advantage of the present invention resides in that complexes with hydrophilic or lipophilic, macrocyclic or open-chain, low-molecular or high-molecular ligands have now become accessible. This affords the possibility of controlling compatibility and pharmacokinetics of these polymer complexes by chemical substitution.

By the choice of suitable bio- or macromolecules (see further below) in V', polymer complexes according to this invention are obtained which exhibit a surprisingly high tissue and organ specificity.

The cascade polymers according to this invention are produced by reacting compounds of general Formula I'

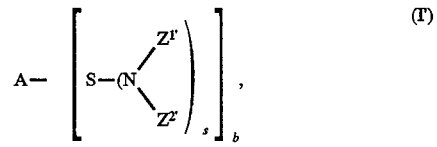

wherein
A means a nitrogen-containing cascade nucleus of the basis multiplicity b,
S means a reproduction unit,
N means a nitrogen atom,
$Z^{1'}$ and $Z^{2'}$ mean the first to penultimate generation, in each case

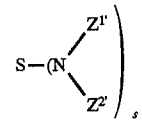

but, for the final generation, in each case mean a hydrogen atom,
b means the numbers 1 through 50, and
s means the numbers 1 to 3,
wherein the reproduction units S need to be identical only for one generation—optionally after reaction of up to 4% of the terminal amino groups with a $C_4$–$C_{20}$-alkylene chain that is substituted at the ends by carboxyl and hydrazide (preferably in the blocked form)—
with a complex or complexing compound K' of the general formulae

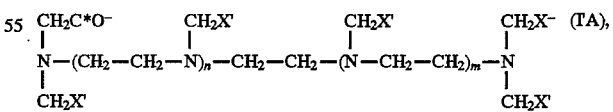

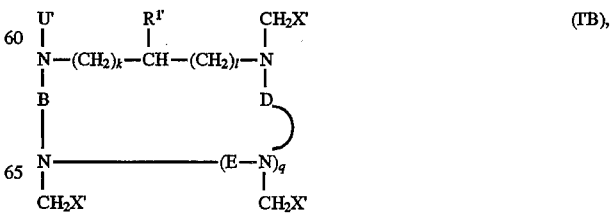

-continued

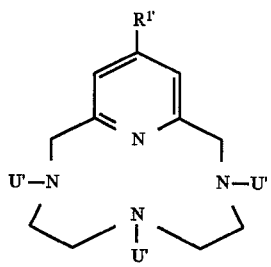
(IC), wherein
n and m in each case are the number 0, 1, 2, 3 or 4, n and m adding up to no more than 4,
k means the number 1, 2, 3, 4 or 5,
l means the number 0, 1, 2, 3, 4 or 5,
q means the number 0, 1 or 2,
U' means —$CH_2C*O$—, $CH_2X'$ or V" wherein V" stands for a straight-chain, branched, saturated or unsaturated $C_1$–$C_{20}$-alkylene group which optionally contains imino, phenylene, phenylenoxy, phenylenimino, amide, hydrazide, ureido, thioureido, carbonyl, ester group(s), oxygen, sulfur and/or nitrogen atom(s) and is optionally substituted by hydroxy, mercapto, imino, epoxy, oxo, thioxo and/or amino group(s), this alkylene group carrying a functional group at the end,
X' means in each case independently the residues —COOH, COOY or V''',
wherein Y is an acid blocking group or a metal ion equivalent of an element of atomic numbers 21–29, 39, 42, 44 or 57–83, and V''' means a substituent to be converted into V',
C*O stands for an activated carbonyl group,
B, D and E, being identical or different, mean in each case the group $(CH_2)_a$ where a means the number 2, 3, 4 or 5,
$R^{1'}$ is V" or a hydrogen atom, with the proviso that $R^{1'}$ stands for V" only if U' means $CH_2X'$ at the same time, and that U' means —$CH_2C*O$— or V" only if $R^{1'}$ means a hydrogen atom at the same time,
optionally splitting off any blocking groups present, reacting, if desired, the thus-obtained cascade polymers—insofar as K' means a completing compound— conventionally with at least one metal oxide or metal salt of an element of atomic numbers 21–29, 39, 42, 44 or 57–83, and optionally converting them into the cascade polymers carrying the desired macro- or biomolecule(s) by conversion of at least one of the —$CO_2H$— or V''' groups contained in K' into the desired alkylene group V" exhibiting a functional group at the end and optionally by subsequent linkage via this functional group and/or via the terminal-positioned hydrazide group that may be contained in $Z^2$, with a macro- or biomolecule and/or by linkage to the biotin or avidin residue, wherein the indicated reaction steps (except for the macro- or biomolecule linkage which can take place only after generating the functional group) can be performed in any desired sequence, and optionally substituting, subsequently, in the thus obtained polymer complexes any still present acidic hydrogen atoms entirely or partially by cations of inorganic and/or organic bases, amino acids or amino acid amides or converting the corresponding acid groups entirely or partially into esters or amides.

Examples of an activated carbonyl group in the complexes and/or complex-forming compounds K' are anhydride, p-nitrophenyl ester and acid chloride.

The alkylation or acylation effected for the introduction of the complex-forming units is carried out with substrates containing the desired substituent K (possibly bound to a leaving group), or from which the desired substituent, optionally after modification by secondary reaction(s), is generated by the reaction. Examples that can be cited for the first-mentioned substrates are halogenides, mesylates, rosylares and anhydrides. Among the second group are, for example, oxiranes, thiiranes, aziranes, α,β-unsaturated carbonyl compounds or their vinylogs, aldehydes, ketones, isothiocyanates and isocyanates.

Examples of secondary reactions that can be mentioned are ester cleavages, hydrogenations, esterifications, oxidations, etherifications and alkylations, performed in accordance with literature methods known to those skilled in the art.

Selected examples of the residues V" contained in K' are listed as follows:

—$CH_2$—CHOH—$CH_2$—NCS;
—$CH_2$—CHOH—$CH_2$—O—$(CH_2)_2$—NCS;
—$CH_2$—CHOH—$CH_2$—O—$(CH_2)_2$—NH—CO—$CH_2$—Br;
—$CH_2$—CHOH—$CH_2$—O—$(CH_2)_2$—O—$(CH_2)_2$—NCS;
—NCS;
—$CH_2$—CHOH—$CH_2$—O—$CH_2$—CHO;
—$CH_2$—CHOH—CHO;

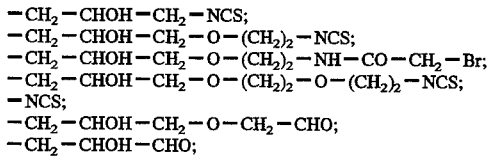

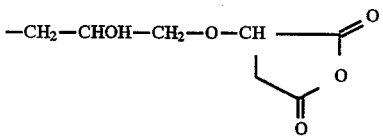

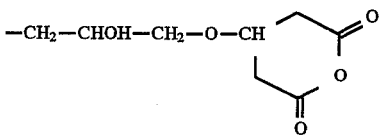

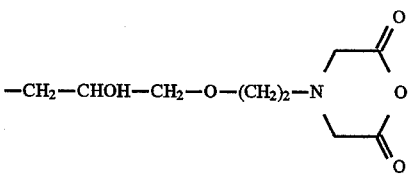

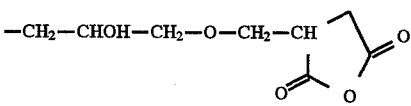

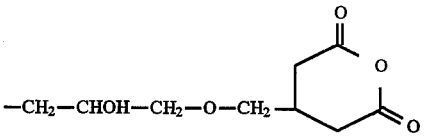

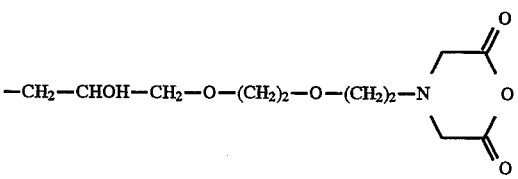

An example that can be cited is the reaction of the monoanhydride $N^3$-(2,6-dioxomorpholinoethyl)-$N^6$-(ethoxycarbonylmethyl)-3,6-diazaoctanedioic acid with the respectively desired cascade polymers, containing terminal amino groups, in water or in mixtures of water with, for example, dioxane, THF, DMF, DMSO or acetonitrile at an alkaline pH, preferably 8–10, i.e. with the addition of bases, such as, for example, sodium hydroxide, potassium hydroxide or triethylamine, at temperatures of 0°–50° C., preferably at room temperature. For a complete reaction, a two- to threefold excess of monoanhydride, for example, is preferably employed.

A further possibility that can be mentioned is the reaction of substituents K' exhibiting terminal-positioned aldehyde groups with the respectively desired cascade polymers containing terminal amino groups, with subsequent reduction of the thus-formed Schiff bases analogously to methods known from the literature (Synthesis 1975, 135). The thus-generated secondary amines can be converted into tertiary amines, amides or thioamides by subsequent acylation or alkylation with α,β-unsaturated esters containing optionally 1–3 carboxy, 1–3 sulfonic acid, 1–5 hydroxy residues and/or 1–3 oxygen atoms, alkyl halogenides, anhydrides, acid halogenides, or complexes and/or complexing compounds K'. As examples of reaction partners which substitute the secondary amino hydrogen atoms the following can be cited: 8r—CH$_2$COOH; Cl—CH$_2$—CH$_2$—COOH; H$_2$C=CH—COOCH$_3$; HOOC—CH=CH—COOCH$_3$; CH$_2$=C (COOEt)—CH$_2$OH; 8r—CH$_2$SO$_3$H; Cl—CH$_2$—CH$_2$—SO$_3$H; CH$_3$—CO—Cl; Cl—CO—CH$_2$OH; Cl—CO—CHOH—CH$_2$OH; ClSO$_2$CH$_3$; ClSO$_2$CH$_2$COOC$_2$H$_5$; 8r—CO—(CHOH)$_4$—CH$_2$OH; Cl—CO—CH$_2$—COOC$_2$H$_5$;

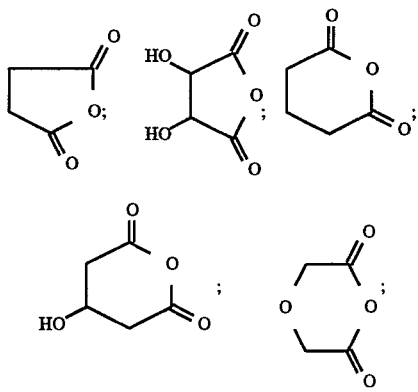

Br—CO—(CH$_2$)$_4$—COOC(CH$_3$)$_3$; Cl—CO—CHOH—COOCH$_3$.

The aldehydes required herein as educts can be prepared from the corresponding vicinal diols by oxidation with, for example, sodium metaperiodate in an aqueous or alcoholic solution analogously to methods known from the literature (e.g. "Makromol. Chem." 182:1641 [1981]).

By pursuing a suitable course of reaction, for example adjusting the pH value or addition of amines, concomitantly introduced ester groups can, if desired, be saponified and aminolyzed, respectively.

Purification of the resultant cascade polymers takes place preferably by ultrafiltration with membranes of a suitable pore size (e.g. "Amicon") or gel filtration on, for example, suitable "Sephadex" gels.

Analogously, for example, complexing compounds or complexes, derived from isothiocyanate, epoxide or α-halogenoacetyl, are made to react under pH control in an aqueous medium with the desired cascade polymer amines.

The compounds I' required as the educts are known (for example, European Patent Applications, Publication Nos. 0,154,788 and 0,331,616, German Patent Application P 38 25 040.3) or they can be prepared from the corresponding polyamines (wherein any present functional groups are optionally blocked) by alkylation with an ester of general Formula II

wherein Hal means chlorine, bromine or iodine and Y' means a hydrogen atom, an alkali metal or an acid blocking group Y.

The reaction takes place in polar aprotic solvents, such as, for example, dimethylformamide, dimethyl sulfoxide, acetonitrile, aqueous tetrahydrofuran or hexamethylphosphoric triamide in the presence of an acid captor, such as, for example, a tertiary amine (e.g. triethylamine, trimethylamine, N,N-dimethylaminopyridine, 1,5-diazabicycl[4.3.0]nonene-5 (DBN), 1,5-diazabicycl[5.4.0] undecene-5 (DBU), alkali, alkaline earth carbonate, bicarbonate or hydroxide (e.g. sodium, magnesium, calcium, barium, potassium carbonate, hydroxide and bicarbonate) at temperatures of between −10° C. and 120° C., preferably between 0° C. and 50° C.

Suitable acid blocking groups Y are lower alkyl, aryl and aralkyl groups, for example the methyl, ethyl, propyl, butyl, phenyl, benzyl, diphenylmethyl, triphenylmethyl, bis(p-nitrophenyl)-methyl groups, as well as trialkylsilyl groups.

The splitting off of the blocking groups Y which may be desirable takes place according to the methods known to one skilled in the art, for example by hydrolysis, hydrogenolysis, alkaline saponification of the esters with an alkali in an aqueous-alcoholic solution at temperatures of 0° C. to 50° C. or, in case of tert-butyl esters, with the aid of trifluoroacetic acid.

Production of the derivatives with an activated carbonyl group C*O, I'A or I'B and I'C wherein U' means CH$_2$C*O (e.g. mixed anhydride, N-hydroxy-succinimide ester, acylimidazoles, trimethylsilyl ester) takes place according to methods known from the literature [Houben-Weyl, "Methoden der organischen Chemie" [Methods of Organic Chemistry], Georg Thieme publishers, Stuttgart, vol. E 5 (1985), 633; Org. React. 12:157 (1962)] or will be described in the experimental portion.

Preparation of the cyclic polyamines needed as educts for I'B and I'C takes place by cyclization of two reactants of which—in case of the synthesis of I'B with $R^{1'}=V''$—one is V'''-substituted, or (in case of the synthesis of I'C) one contains the desired 6-membered ring of the final product or a precursor to be converted into this ring.

The cyclization is carried out according to methods known from the literature [for example, Org. Synth. 58:86 (1978), Macrocyclic Polyether Syntheses, Springer publishers, Berlin, Heidelberg, New York (1982), Coord. Chem. Rev. 3:3 (1968), Ann. Chem. 1976:916, J. Org. Chem. 49:110 (1984)]; one of the two reactants carries two leaving groups at the chain end, the other carries two nitrogen atoms which displace these leaving groups in nucleophilic fashion. An example that can be cited is the reaction of terminal-positioned dichloro, dibromo, dimesyloxy, ditosyloxy or dialkoxycarbonyl alkylene compounds, containing, if desired, the substituent V''' and optionally one to five nitrogen atom(s), with terminal-positioned polyazaalkylene compounds optionally containing one to five additional nitrogen atom(s) in the alkylene chain. The substituent V''' can, instead, also be contained in the second reactant, i.e. the one having the terminal-positioned nucleophilic nitrogen atoms. The nitrogen atoms are blocked, if necessary, for example as tosylates or trifluoroacetates, and they are liberated according to methods known in the literature prior to the subsequent alkylation reaction (the tosylates, for example, with mineral acids, alkali metals in liquid ammonia, hydrobromic acid and phenol, "RedAl", lithium aluminum hydride, sodium amalgam, compare, for example, Liebigs Ann. Chem. 1977:1344, Tetrahedron Letters 1976:3477; the trifluoroacetates, for example, with mineral acids or ammonia in methanol, compare, for example, Tetrahedron Letters 1967:289).

For preparing macrocycles differently substituted on the nitrogen atoms (hydrogen or the group CH$_2$COOY), these atoms can be provided in the educts with differing blocking groups, for example with tosylate and benzyl groups. The latter are then likewise removed according to methods known in the literature (preferably by hydrogenation, e.g. EP Patent Application 232,751).

In case diesters are used in the cyclization reaction, the resultant diketo compounds must be reduced by methods known to a person skilled in the art, for example with diborane.

It is also possible to cyclize correspondingly substituted terminal-positioned bisaldehydes with the respectively desired terminal-positioned bisamines; the reduction of the thus-obtained Schiff bases takes place according to methods known in the literature, for example by catalytic hydrogenation [Helv. Chim. Acta 61:1376 (1978)].

The amines required to serve as starting materials for the cyclization are prepared in analogy to methods known from the literature.

Starting with an N-blocked amino acid, reaction with a partially blocked diamine (e.g. according to the carbodiimide method), splitting off of the blocking groups, and diborane reduction yield a triamine.

Reaction of a diamine obtained from amino acids [Eur. J. Med. Chem.-Chim. Ther. 21:333 (1986)] with twice the molar amount of an N-protected ω-amino acid yields a tetramine after appropriate working up procedure.

The desired diamines can also be prepared by Gabriel reaction from, for example, the corresponding tosylates or halogenides [compare, for example, Inorg. Chem. 25:4781 (1986)].

In both cases, the number of carbon atoms between the N atoms can be determined by the type of diamines or amino acids utilized as coupling partners.

Conversion of a precursor of I'C, obtained by cyclizing, into the desired complexing compound takes place according to methods known to one skilled in the art, for example deoxygenation of nitroxide [E. Klingsberg, The Chemistry of Heterocyclic Compounds, vol. 14, part 2, Interscience Publishers, New York, page 120, 1961) rings, conversions, and introduction of functional groups at the pyridine ring, e.g. liberation of phenolic hydroxy groups [J. Org. Chem. 53:5 (1988)], introduction of halogen substituents [E. Klingsberg, The Chemistry of Heterocyclic Compounds, vol. 14, part 2, Interscience Publishers, New York, page 341, 1961; Houben-Weyl, "Methoden der organischen Chemie", vol. V/3, 651 (1962)].

Functionalization of 4-halopyridine derivatives (e.g. azide exchange) in the phase transfer process with the use of 18-crown-6 or tetrabutylammonium halogenide as the catalyst has been described in "Phase Transfer Reactions" (Fluka Compendium vol. 2, Walter E. Keller, Georg Thieme publishers, Stuttgart, N.Y.). A thus-obtained azide group can be converted into an amino function in accordance with methods known to one skilled in the art (e.g. catalytic hydrogenation, Houben-Weyl, "Methoden der organischen Chemie", vol. 11/1, p. 539; or reaction with Raney nickel/hydrazine, German Patent Application 3,150,917). This amino function can be converted into an isothiocyanate group according to methods known from the literature (for example with thiophosgene in a two-phase system, S. Scharma, Synthesis 1978:803; D. K. Johnson, J. Med. Chem. 1989, vol. 32, 236).

By reacting an amino function with a haloacetic acid halogenide, an α-halogenoacetamide group can be generated (JACS 1969, vol. 90, 4508; Chem. Pharm. Bull. 29 (1):128, 1981) which is suitable for coupling to bio- or macromolecules or cascade polymers in the same way as, for example, the isothiocyanate group.

As a substituent V''' which can be converted into V, or into the substituent V'' exhibiting at the end a functional group suitable for linking to a macro- or biomolecule or to a cascade polymer, suitable are, inter alia, hydroxy and nitrobenzyl, hydroxy and carboxyalkyl, as well as thioalkyl residues of up to 20 carbon atoms. They are converted, according to literature methods known to one skilled in the art [Chem. Pharm. Bull. 33:674 (1985), Compendium of Org. Synthesis, vol. 1–5, Wiley and Sons, Inc., Houben-Weyl, "Methoden der organischen Chemie", vol. VIII, Georg Thieme publishers, Stuttgart, J. Biochem. 92:1413 (1982)], into the desired substituents (e.g. with the amino, hydrazino, hydrazinocarbonyl, epoxide, anhydride, methacryloylhydrazinocarbonyl, maleimidamidocarbonyl, halo, halocarbonyl, mercapto, isothiocyanate group as the functional group) where, in case of the nitrobenzyl residue, first a catalytic hydrogenation to the aminobenzyl derivative must be performed (for example according to P. N. Rylander, Catalytic Hydrogenation Over Platinum Metals, Academic Press, 1967).

Examples of the conversion of hydroxy or amino groups bound to aromatic or aliphatic residues are the reactions carried out with a substrate of general Formula III $$Nf\text{-}L\text{-}Fu \quad (III)$$

wherein

Nf means a nucleofugal entity, such as, for example, Cl, Br, I, $CH_3C_6H_4SO_3$ or $CF_3SO_3$, L is an aliphatic, aromatic, arylaliphatic, branched, straight-chain or cyclic hydrocarbon residue of up to 20 carbon atoms, and Fu is the desired, terminal-positioned functional group, optionally in the blocked form (DOS 3,417,413), performed in suitable solvents, such as tetrahdyrofuran, dimethoxyethane or dimethyl sulfoxide, two-phase aqueous systems, such as, for example, water/dichloromethane, in the presence of an acid captor, such as, for example, sodium hydroxide, sodium hydride or alkali or alkaline earth carbonates, such as, for example, sodium, magnesium, potassium, calcium carbonate or poly-(4-vinylpyridine) "Reillex", at temperatures of between 0° C. and the boiling point of the respective solvent, but preferably between 20° C. and 60° C.

Examples of compounds according to general Formula III are:

$Br(CH_2)_2NH_2$, $Br(CH_2)_3OH$, $BrCH_2COOCH_3$, $BrCH_2CO_2{}^tBu$, $ClCH_2CONHNH_2$, $Br(CH_2)_4CO_2C_2H_5$, $BrCH_2COBr$, $BrCH_2CONH_2$, $ClCH_2COOC_2H_5$, $BrCH_2CONHNH_2$,

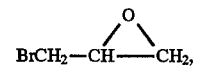

$CF_3SO_3(CH_2)_3Br$, $BrCH_2C\equiv CH$, $BrCH_2CH=CH_2$.

Conversions of carboxy groups can be performed, for example, according to the carbodiimide method (Fieser, Reagents for Organic Syntheses 10, 142), by way of a mixed anhydride [Org. Prep. Proc. Int. 7:215 (1975)] or by way of an activated ester (Adv. Org. Chem., part B, 472).

Introduction of the optionally desired substituent V'' at a nitrogen atom of the complexing compounds I'B and I'C (i.e., U'=V'') can likewise be effected according to the above-mentioned process, i.e. here, too, a macrocycle intermediate stage containing V''' is usually passed through which is obtained by reaction of a polyaza macrocycle exhibiting only one free NH group. Examples in this connection are the reaction of, for example, 1,4,7-triscarboxymethyl-1,4,7,10-tetraazacyclocodecane with a primary epoxide exhibiting a blocked amino group, subsequent liberation of the amino function of the resultant V'''-substituted macrocycle, and subsequent conversion into a V''-substituted macrocycle (for example, conversion of the amino group into a functional group that can be coupled to the cascade polymer amine, such as, for example, the isothiocyanate or 2-halogenoacetamide group).

The cascade polymers carrying terminal amino groups, needed for coupling to the complexing compounds K (and/ or also the corresponding metal-containing complexes), are prepared according to methods known to persons skilled in the art by a cascade-type, generation-wise introduction of nitrogen atoms into a nitrogen-containing basis molecule. This yields a generation from at least two reaction steps. From each amino hydrogen atom of the cascade starter, up to three amino groups are generated in this way by, for example, a Michael addition or addition of a primary epoxide containing a suitable functional group, and subsequent conversion of the thus-introduced functional group.

An example that can be cited is the substitution of the six amino hydrogen atoms of the cascade starter tris (aminoethyl)amine by six —$CH_2CH_2$—CONH—$CH_2CH_2NH_2$ units obtained by Michael addition with acrylic acid ester and subsequent aminolysis with ethylenediamine. The aminolysis, preferably performed without solvents, is here conducted with an up to 500-fold amine excess per ester grouping at temperatures of 0° C. to about 130° C.

As an example of an epoxide addition, the reaction can be cited of 6,6',6'',6''',6'''',6'''''-hexaamino-6,6',6'',6''',6'''',6'''''-hexadeoxy-α-cyclodextrin with 1,3-(N,N'-tetrabenzyl) diamino-2-(oxiranylmethoxy) propane and subsequent liberation of the amino functions by catalytic hydrogenation in accordance with methods known to one skilled in the art (see also above).

A portion of the acid groups of the thus-obtained polymer compounds, introduced via the complex forming units K, can be further functionalized, if desired, according to processes known to a person skilled in the art, for example by converting into ester, amide, hydrazide, maleimido or other groups suitable for coupling to bio- or macromolecules.

The thus-obtained complexing ligands (as well as the complexes) can also be linked to bio- or macromolecules from which it is known that they are particularly accumulated in the organ or organ part to be examined. Such molecules are, for example, enzymes, hormones, polysaccharides, such as dextrans or starches, porphyrins, bleomycins, insulin, prostaglandins, steroid hormones, amino sugars, amino acids, peptides such as polylysine, proteins (such as, for example, immunoglobulins, monoclonal antibodies, lectins), lipids (also in the form of liposomes), and nucleotides of the DNA or RNA type. Especially to be emphasized are conjugates with albumins, such as human serum albumin, antibodies, e.g. monoclonal antibodies specific for tumor-associated antigens, or antimyosin. Instead of biological macromolecules, it is also possible to link suitable synthetic polymers, such as polyethylenimines, polyamides, polyureas, polyethers, such as polyethylene glycols, and polythioureas. The pharmaceutical agents formed therefrom are suitabe, for example, for use in tumor and infarction diagnostics, as well as tumor therapy. Monoclonal antibodies (e.g. Nature 256:495, 1975) have the advantages over polyclonal antibodies that they are specific for an antigen determinant, that they possess definite binding affinity, that they are homogeneous (thus substantially simplifying their production in pure form), and that they can be manufactured in large amounts in cell cultures. Suitable are, for example, for tumor imaging, monoclonal antibodies and/or their fragments Fab and F(ab')$_2$ which are specific, for example, for human tumors of the gastrointestinal tract, of the breast, of the liver, of the bladder, of the gonads, and of melanomas [Cancer Treatment Repts. 68:317 (1984), Bio. Sci. 34:150 (1984)] or are directed against carcinomembryonal antigen (CEA), human chorionic gonadotropin (β-HCG), or other tumor-positioned antigens, such as glycoproteins [New Engl. J. Med. 298:1384 (1973), U.S. Pat. No. 4,331,647]. Suitable are, inter alia, also antimyosin, anti-insulin and antifibrin antibodies (U.S. Pat. No. 4,036, 945).

Colon carcinomas can be confirmed by NMR diagnosis with the aid of conjugates complexed with gadolinium(III) ions, using the antibody 17-1A (Centocor, USA).

For liver examinations and tumor diagnostics, respectively, conjugates or inclusion compounds are suitable, for example, with liposomes utilized, for instance, as unilamellar or multilamellar phosphatidylcholine cholesterol vesicles.

Heretofore, bonding of metals to the desired macro- or biomolecules has been performed according to methods described, for example, in Rev. Roum. Morphol. Embryol. Physio., Physiologie 1981, 18:241, and in J. Pharm. Sci. 68:79 (1979), e.g. by reaction of the nucleophilic group of a macromolecule, such as the amino, phenol, sulfhydryl, aldehyde or imidazole group, with an activated derivative of the polymer complex or ligand. Examples of activated derivatives are anhydrides, acid chlorides, mixed anhydrides (see, for example, G. E. Krejcarek and K. L. Tucker, Biochem., Biophys. Res. Commun. 1977, 581), activated esters, nitrenes or isothiocyanates. Conversely, it is also possible to react an activated macromolecule with the polymer complex or ligand. For conjugation with proteins, also suitable are, for example, substituents of the structure $C_6H_2N_2^+$, $C_6H_4NHCOCH_2Br$, $C_6H_4NCS$ or $C_6H_4OCH_2COBr$.

However, this type of linkage is burdened by the drawback of lack in complex stability of the conjugates and/or lack of specificity (for instance, Diagnostic Imaging 84:56; Science 220:613, 1983; Cancer Drug Delivery 1:125, 1984). The conjugate formation according to the present invention takes place, in contrast thereto, via the functional groups present in V'. It is possible herein to bind up to more than one-hundred metal ions via one binding site in the macromolecule.

In case of the antibody conjugates, binding of the antibody to the complex or ligand must not lead to loss or reduction of binding affinity and binding specificity of the antibody to the antigen. This can be accomplished either by binding to the carbohydrate portion in the Fc part of the glycoprotein and/or in the Fab or F(ab')$_2$ fragments, or by binding to sulfur atoms of the antibody and/or antibody fragments.

In the first instance, an oxidative cleavage of sugar units must first be performed for the generation of formyl groups capable of coupling. This oxidation can be carried out by chemical methods with oxidizing agents such as, for example, periodic acid, sodium metaperiodate, or potassium metaperiodate in accordance with methods known from the literature (e.g., J. Histochem. and Cytochem. 22:1084, 1974) in an aqueous solution in concentrations of 1–100 mg/ml, preferably 1–20 mg/ml, and with a concentration of the oxidizing agent of between 0.001 to 10 millimoles, preferably 1 to 10 millimoles, in a pH range of about 4 to 8 at a temperature of between 0° and 37° C. and with a reaction period of between 15 minutes and 24 hours. The oxidation can also be performed by enzymatic methods, for example with the aid of galactose oxidase in an enzyme concentration of 10–100 units/ml, a substrate concentration of 1–20 mg/ml, at a pH of 5 to 8, a reaction period of 1–8 hours, and a temperature of between 20° and 40° C. (for example, J. Biol. Chem. 234:445, 1959).

Complexes or ligands with suitable functional groups, such as, for example hydrazine, hydrazide, hydroxylamine, phenylhydrazine, semicarbazide and thiosemicarbazide, are bound to the aldehydes generated by oxidation; this is done by reacting between 0° and 37° C. with a reaction period of 1–65 hours, a pH of between about 5.5 and 8, an antibody concentration of 0.5–20 mg/ml, and a molar ratio of the complexing compound to the antibody aldehyde of 1:1 to 1000:1. The subsequent stabilization of the conjugate takes place by reduction of the double bond, for example with sodium borohydride or sodium cyanoborohydride; the reducing agent is utilized herein with a 10- to 100-fold excess (e.g., J. Biol. Chem. 254:4359, 1979).

The second possibility of forming antibody conjugates starts with a gentle reduction of the disulfide bridges of the immunoglobulin molecule; in this process, the more sensitive disulfide bridges between the H chains of the antibody molecule are cleaved whereas the S—S bonds of the antigen-binding region remain intact so that there is practically no reduction in binding affinity and specificity of the antibody (Biochem. 18:2226, 1979; Handbook of Experimental Immunology, vol. 1, 2nd ed., Blackwell Scientific Publications, London 1973, chapter 10). These free sulfhydryl groups of the inter-H-chain regions are then reacted with suitable functional groups of complexing compounds or metal complexes at 0°–37° C., a pH of about 4–7, and a reaction period of 3–72 hours with the formation of a covalent bond which does not affect the antigen binding region of the anti-body. Suitable reactive groups are, for example: haloalkyl, haloacetyl, p-mercuribenzoate, isothiocyanate, thiol, epoxy groups, as well as groups to be subjected to a Michael addition reaction, such as, for example, maleinimides, methacrylo groups (e.g. J. Amer. Chem. Soc. 101:3097, 1979).

Additionally, for linking the antibody fragments with the polymer complexes or with the ligands, there is a number of suitable bifunctional "linkers" which are frequently also obtainable commercially (see, for example, Pierce, Handbook and General Catalogue 1986) which are reactive with respect to the SH groups of the fragments as well as with respect to the amino or hydrazino groups of the polymers.

Examples that can be cited are:
m-maleimidobenzoyl-N-hydroxysuccinimide ester (MBS),
m-maleimidobenzoyl-N-sulfosuccinimide ester (Sulfo-MBS),
N-succinimidyl-[4-(iodoacetyl)amino]benzoic acid ester (SIAB),
succinimidyl-4-(N-maleimidomethyl)cyclohexane-1-carboxylic acid ester (SMCC),
succinimidyl-4-(p-maleimidophenyl)butyric acid ester (SMPB),
N-succinimidyl-3-(2-pyridyldithio)propionic acid ester (SDPD),
4-[3-(2,5-dioxo-3-pyrrolinyl)propionyloxy]-3-oxo-2,5-diphenyl-2,3-dihydrothiophene-1,1-dioxide,
acetylalanylleucylalanylaminobenzyl,
acetamido-p-thioureidobenzyl.

It is also possible to utilize bonds not of the covalent type for coupling purposes wherein ionic as well as van der Waals and hydrogen bridge bonds can contribute toward the linkage in varying proportions and strengths (key and lock principle) (for example, avidin-biotin, antibody-antigen). Also inclusion compounds (host-guest) of relatively small complexes in relatively large cavities in the macromolecule are possible.

The coupling principle resides in first producing a bifunctional macromolecule by either fusing an antibody hybridoma directed against a tumor antigen with a second antibody hybridoma directed against a complex according to this invention, or linking the two antibodies chemically via a linker (e.g. in the way set forth in J. Amer. Chem. Soc. 101:3097, 1979) or binding the antibody directed against the tumor antigen to avidin (or biotin, respectively), optionally via a linker [D. J. Hnatowich et al., J. Nucl. Med. 28:1294 (1987)]. In place of the antibodies, it is also possible to employ their corresponding F(ab) or F(ab')$_2$ fragments. For pharmaceutical usage, first the bifunctional macromolecule is injected which is accumulated at the target site, and then, at a time interval, the complex compound of this invention is injected [optionally bound to biotin (or avidin)] which is coupled on at the target site in vivo and there can deploy its diagnostic or therapeutic activity. Moreover, other coupling methods can likewise be utilized, such as, for example, "reversible radiolabeling" described in Protein Tailoring Food Med. Uses [Am. Chem. Soc. Symp. 349 (1985)].

A particularly simple method for the production of antibody conjugates or antibody fragment conjugates is available in the form of the so-called solid phase coupling procedure: The antibody is coupled to a stationary phase (e.g. an ion exchanger) located, for example, in a glass column. By successive flushing of the column with a solution suitable for generation of aldehyde groups, washing, rinsing with a solution of the functionalized complex (or ligand), washing (in case the ligand is used, rinsing is furthermore performed with a solution containing the metal salt, followed by another rinsing step) and, finally, elution of the conjugate, very high conjugate yields are obtained.

This procedure permits the automatic and continuous production of any desired quantities of conjugates.

Also other coupling steps can be performed in this way.

Thus, for example, fragment conjugates can be prepared by the sequence of papain reduction/bifunctional linker/functionalized complex or ligand.

The thus-formed compounds are subsequently purified preferably by chromatography by way of ion exchangers on a fast protein liquid chromatography unit.

The metal complexes of this invention are produced as disclosed in German Laid-Open Application 3,401,052 by dissolving or suspending the metal oxide or a metallic salt (e.g. the nitrate, acetate, carbonate, chloride or sulfate) of the element of atomic numbers 21–29, 42, 44, 57–83 in water and/or in a lower alcohol (such as methanol, ethanol or isopropanol), and reacting with a solution or suspension of the equivalent amount of the complexing ligand and subsequently, if desired, substituting any acidic hydrogen atoms present in the acid or phenol groups by cations of inorganic and/or organic bases or amino acids.

Introduction of the desired metal ions can take place at the stage of the complexing compounds I'A, I'B or I'C, i.e. prior to coupling to the cascade polymers, as well as after the coupling of the unmetalated ligands I'A, I'B or I'C.

Neutralization takes place herein with the aid of inorganic bases (e.g. hydroxides, carbonates or bicarbonates) of, for example, sodium, potassium, lithium, magnesium or calcium and/or organic bases, such as, inter alia, primary, secondary and tertiary amines, e.g. ethanolamine, morpholine, glucamine, N-methyl- and N,N-dimethylglucamine, as well as basic amino acids, such as, for example, lysine, arginine and ornithine, or of amides from originally neutral or acidic amino acids.

In order to prepare the neutral complex compounds, it is possible, for example, to add to the acidic complex salts in an aqueous solution or suspension such an amount of the desired bases that the neutral point is obtained. The resultant solution can then be concentrated to dryness under vacuum. It is frequently advantageous to precipitate the thus-formed neutral salts by adding water-miscible solvents, e.g. lower alcohols (methanol, ethanol, isopropanol and others), lower ketones (acetone and others), polar ethers (tetrahydrofuran, dioxane, 1,2-dimethoxyethane and others) and to obtain in this way crystallized products which can be easily isolated and readily purified. It proved to be especially-advantageous to add the desired base as early as during the complex formation to the reaction mixture and thereby to save a process step.

In case the acidic complex compounds contain several free acidic groups, it is frequently expedient to produce neutral mixed salts containing inorganic as well as organic cations as the counterions.

This can be done, for example, by reacting the complex forming ligand in an aqueous suspension or solution with the oxide or salt of the element yielding the central ion, and with half the amount of an organic base required for neutralization; isolating the thus-formed complex salt; purifying same if desired; and then combining, for complete neutralization, with the needed amount of inorganic base. The sequence of addition of the bases can also be reversed.

Another possibility of obtaining neutral complex compounds resides in converting the remaining acid groups in the complex entirely or partially into esters or amides, for example. This can be done by subsequent reaction at the finished polymer complex (e.g. by exhaustive reaction of the free carboxy groups with dimethyl sulfate), as well as also by the use of a suitably derivatized substrate for introducing the complexing units of general Formulae I'A, I'B and I'C (e.g. $N^3$-(2,6-dioxomorpholinoethyl)-$N^6$-(ethoxycarbonylmethyl)-3,6-diazaoctanedioic acid).

The conjugates of antibody and complex are dialyzed, prior to in vivo use, after incubation with a weak complexing agent, such as, for example, sodium citrate, sodium ethylenediaminetetraacetic acid, in order to remove weakly bound metal atoms.

The pharmaceutical agents of this invention are likewise produced in a manner known per se by suspending or dissolving the complex compounds of this invention—optionally combined with the additives customary in galenic pharmacy—in an aqueous medium and then optionally sterilizing the suspension or solution. Suitable additives are, for example, physiologically acceptable buffers (such as, for instance, tromethamine), additions of complexing agents (e.g. diethylenetriaminepentaacetic acid) or—if required—electrolytes, e.g. sodium chloride or—if necessary—antioxidants, such as ascorbic acid, for example.

If suspensions or solutions of the compounds of this invention in water or physiological saline solution are desirable for enteral administration or other purposes, they are mixed with one or several of the auxiliary agents (e.g. methylcellulose, lactose, mannitol) and/or tensides (e.g. lecithins, "Tween", "Myrj") and/or flavoring agents to improve taste (e.g. ethereal oils), as customary in galenic pharmacy.

In principle, it is also possible to produce the pharmaceutical agents of this invention without isolating the complex salts. In any event, special care must be taken to effect chelate formation so that the salts and salt solutions according to this invention are practically devoid of uncomplexed, toxically active metal ions.

This can be ensured, for example, with the aid of dye indicators, such as xylenol orange, by control titrations during the manufacturing process. Therefore, the invention also concerns processes for the production of the complex compounds and their salts. A final safety measure resides in purifying the isolated complex salt.

The pharmaceutical agents of this invention preferably contain 1 μmol to 1 mol/l of the complex salt and are normally made into doses in amounts of 0.0001–5 mmol/kg. They are intended for enteral and parenteral administration. The complex compounds according to this invention are utilized (1) for NMR and X-ray diagnostics in the form of their complexes with the ions of the elements with atomic numbers 21–29, 39, 42, 44 and 57–83;

(2) for radiodiagnostics and radiotherapy in the form of their complexes with the radioisotopes of the elements with atomic numbers 27, 29, 31, 32, 37–39, 43, 49, 62, 64, 70, 75 and 77.

The agents of this invention meet the variegated requirements for being suitable as contrast media for nuclear spin tomography. Thus, they are excellently suited for improving the informative content of the image obtained with the aid of the NMR tomograph upon oral or parenteral administration, by increasing the signal intensity. Furthermore, they exhibit the high efficacy necessary to introduce into the body a minimum amount of burdening foreign substances, and they show the good compatibility required for maintaining the noninvasive character of the examinations.

The good water solubility and low osmolality of the compounds of this invention make it possible to prepare highly concentrated solutions, thus maintaining the volume load on the circulation within tolerable limits and compensating for dilution by body fluid, i.e. NMR diagnostic aids must exhibit. 100–1,000 times the water solubility of agents for NMR spectroscopy. Furthermore, the agents of this invention exhibit not only a high in vitro stability but also a surprisingly high stability in vivo so that release or exchange of the ions—actually toxic—not bound in a covalent fashion in the complexes takes place only extremely gradually within the time period during which the novel contrast media are again completely eliminated.

In general, the agents of this invention are used, for NMR diagnostic aids, in doses amounting to 0.0001–5 mmol/kg, preferably 0.005–0.5 mmol/kg. Details of use are discussed, for example, in H. J. Weinmann et al., Am. J. of Roentgenology 142:619 (1984).

Especially low doses (below 1 mg/kg body weight) of organ-specific NMR diagnostic aids are usable, for example, for the detection of tumors and of cardiac infarction.

Furthermore, the complex compounds according to this invention can be employed with advantage as susceptibility reagents and as shift reagents for in vivo NMR spectroscopy.

The agents of this invention, based on their favorable readioactive properties and good stability of the complex compounds contained therein, are also suited as radiodiagnostic agents. Details of their usage and dosage are described, for example, in "Radiotracers for Medical Applications", CRC Press, Boca Raton, Fla.

Another imaging method with radioisotopes is the positron emission tomography, using positron-emitting isotopes, such as, for example, $^{43}$Sc, $^{44}$Sc, $^{52}$Fe, $^{55}$Co and $^{68}$Ga (Heiss, W. D.; Phelps, M. E.: Positron Emission Tomography of Brain, Springer publishers, Berlin, Heidelberg, N.Y. 1983).

The compounds of this invention can also be utilized in radioimmuno- or radiation therapy. This process differs from the corresponding diagnostics only in the quantity and type of isotope employed. The objective herein is the destruction of tumor cells by high-energy shortwave radiation with a minimum range. Suitable β-emitting ions are, for example, $^{46}$Sc, $^{47}$Sc, $^{48}$Sc, $^{72}$Ga, $^{73}$Ga and $^{90}$Y. Suitable s-emitting ions exhibiting short half-life periods are, for example, $^{211}$Bi, $^{212}$Bi, $^{213}$Bi and $^{214}$Bi, wherein $^{212}$Bi is preferred. A suitable ion emitting photons and electrons is $^{158}$Gd which can be obtained from $^{157}$Gd by neutron capture.

If the agent of this invention is intended for use in the version of radiation therapy proposed by R. L. Mills et al. [Nature, vol. 336:787 (1988)], then the central ion must be derived from a Mössbauer isotope, such as, for example, $^{57}$Fe or $^{151}$Eu.

In the in vivo administration of the therapeutic agents according to this invention, they can be given together with a suitable carrier, e.g. serum or physiological sodium chloride solution and together with another protein, such as, for example, human serum albumin. The dosage herein is dependent on the type of cellular disorder, the metal ion used, and the type of imaging method.

The therapeutic media of this invention are, e.g., administered parenterally, preferably intravenously.

Details of usage of radiotherapeutic agents. are discussed, for example, in R. W. Kozak et al., TIBTEC, October 1986, 262.

The agents of this invention are excellently suited as X-ray contrast media; in this connection, it is to be especially emphasized that they reveal no indication of anaphylaxis-type reactions, known from iodine-containing contrast media, in biochemical-pharmacological studies. They are particularly valuable, on account of the favorable absorption properties in regions of higher tube voltages, for digital subtraction techniques.

In general, the agents of this invention are utilized, for administration as X-ray contrast media, analogously to, for example, meglumine diatrizoate, in doses amounting to 0.1–5 mmol/kg, preferably 0.25–1 mmol/kg.

Details of utilization of X-ray contrast media are discussed, for example, in Barke, "Röntgenkontrastmittel" [X-Ray Contrast Media], G. Thieme, Leipzig (1970) and P. Thurn, E. Bücheler, "Einführung in die Röntgendiagnostik" [Introduction to X-Ray Diagnostics], G. Thieme, Stuttgart, New York (1977).

In summation, the synthesis has been accomplished of novel complexing compounds, metal complexes and metal complex salts, opening up new possibilities in diagnostic and therapeutic medicine. This development appears to be desirable, above all in light of the evolution of novel imaging methods in medical diagnostics.

(a) Without contrast medium: The signal intensity of the image is almost zero due to suppression of all tissues with relatively long $T_1$ times.

(b) One second after administration of 0.1 mmol Gd/kg of the title compound of Example 8: on account of intravasal distribution of the contrast medium, only the $T_1$ time of the blood is extremely shortened so that the signal intensity of the blood, in contrast to the surrounding tissue, is correspondingly high, and the result is an excellent contrasting of the vessels.

(c) and (d) Four and, respectively, 10 minutes after administration of the title compound of Example 8: in correspondence with the excretion of the compound, shortening of the $T_1$ time of the signal intensity drops again.

Figure 3:
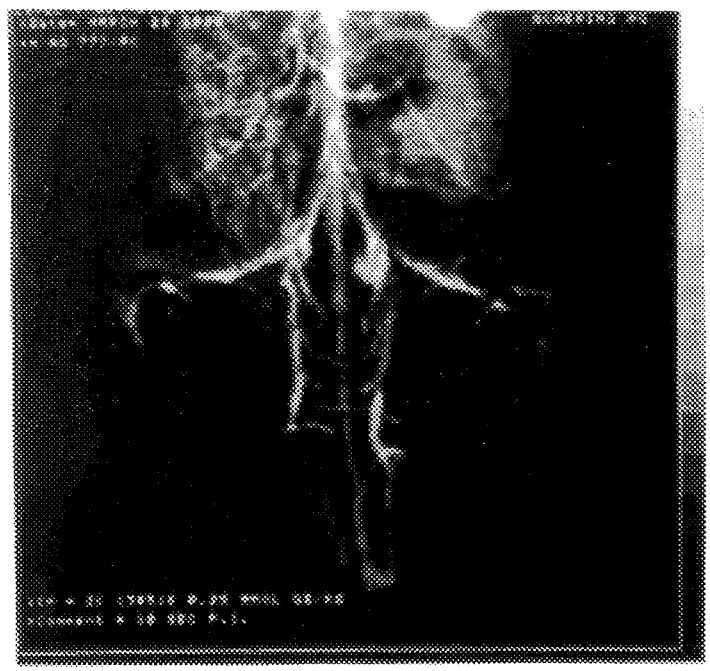

FIG. 3: Coronary projection image of the abdominal region of a rat ten seconds after administration of the title compound of Example 8 (0.25 mmol Gd/kg). All of the significant blood vessels can clearly be observed. A tumor is located in the zone of the left thigh (on the right-hand side as seen by the observer), modifying the vascular structure.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, if any, cited above and below, and of corresponding application Federal Republic of Germany P 39 38 992.8, filed Nov. 21, 1989, are hereby incorporated by reference.

EXAMPLE 1

(a) 1,2-Epoxy-3-dibenzylaminopropane

At 0° C., 100 g (506.9 millimoles) of dibenzylamine (dissolved in 300 ml of methylene chloride) is added dropwise to a thoroughly stirred suspension of 234.51 g (2.53 mol) of epichlorohydrin and 200 ml of 32% sodium hydroxide solution. The mixture is stirred for 2 hours at 0° C. and then 3 hours at room temperature. The mixture is diluted with 3 l of water and extracted 3 times with 500 ml of methylene chloride. The organic phases are combined, dried over magnesium sulfate, and evaporated under vacuum. The remaining oil is flash-chromatographed on silica gel (mobile phase: methylene chloride/hexane/acetone:20/10/3). Yield: 111.72 g of a colorless oil (87% of theory).

Analysis: C 80.60 H 7.56 N 5.53 (Calcd.) C 80.62 H 7.50 N 5.48 (Found)

(b) 10-(3-Dibenzylamino-2-hydroxypropyl)-1,4,7-triscarboxymethyl-1,4,7,10-tetraazacyclododecane 20 g (78.95 mmol) of the title compound of Example 1(a) and 20.51 g (59.21 mmol) of 1,4,7-triscarboxymethyl-1,4,7,10-tetraazacyclododecane (= DO3A) are dissolved in a mixture of 50 ml of dioxane/200 ml of water, and the pH value is brought to 10 with 6N potassium hydroxide solution. The mixture is stirred for 24 hours at 40° C., evaporated to dryness, the residue taken up with 500 ml of water/500 ml of methanol, and extracted twice with 200 ml of tert-butylmethyl ether. The aqueous solution is adjusted to pH 3 with 5N hydrochloric acid and evaporated to dryness. The residue is concentrated under vacuum and then passed on to a column of poly-(4-vinylpyridine). The product is eluted with a solution of ethanol/water 1:1. After evaporation under vacuum, 22.37 g (63% of theory, based on DO3A) of the title compound is obtained as a highly hygroscopic, vitreous solid (6.9% of water per analysis).

Analysis: C 62.08 H 7.56 N 11.68 (Calcd.) C 62.15 H 7.61 N 11.61 (Found)

(c) Gadolinium Complex of 10-(3-Dibenzylamino-2-hydroxypropyl)-1,4,7-triscarboxymethyl-1,4,7,10-tetraazacyclododecane 21 g (35.02 mmol) of the title compound of Example 1(b) is dissolved in a solution of 150 ml of deionized water/50 ml of methanol, and 6.35 g (17.51 mmol) of gadolinium oxide is added thereto. The mixture is refluxed for 2 hours, and 3 g of activated carbon is added. The solution is filtered in the hot state, and the filtrate is evaporated to dryness under vacuum. Yield: 25.08 g (95% of theory) of a vitreous solid (5.2% water per analysis).

Analysis: C 49.39 H 5.61 N 9.29 Gd 20.86 (Calcd.) C 49.41 H 5.70 N 9.25 Gd 20.88 (Found)

(d) Gadolinium Complex of 10-(3-Amino-2-hydroxypropyl)-1,4,7-triscarboxymethyl-1,4,7,10-tetraazacyclododecane 24 g (31.83 mmol) of the title compound of Example 1(c) is dissolved in a mixture of 250 ml of deionized water/150 ml of methanol, and 10 g of palladium catalyst (10% Pd on active carbon) is added. The mixture is then hydrogensted for 24 hours at 50° C., filtered off from the catalyst, and the filtrate is evaporated under vacuum. Yield: 17.89 g (98% of theory) of the title compound as a vitreous solid (6.4% water per analysis).

Analysis: C 35.59 H 5.27 N 12.21 Gd 27.41 (Calcd.) C 35.51 H 5.34 N 12.16 Gd 27.36 (Found)

(e) Gadolinium Complex of 10-(3-Isothiocyanato-2-hydroxypropyl)-1,4,7-triscarboxymethyl-1,4,7,10-tetraazacyclododecane A solution of 4.81 g (41.83 mmol) of thiophosgene in 100 ml of chloroform is added to a solution of 12 g (20.92 mmol) of the title compound of Example 1(d) in 500 ml of deionized water and 20 ml of polyvinylpyridine (Reillex). The two-phase solution is stirred for 10 minutes at 40° C., then for one hour at room temperature, and filtered. The organic phase is separated and the aqueous phase extracted additionally twice with 200 ml of chloroform. The aqueous phase is then freeze-dried. Yield: 12.62 g (98% of theory) of a colorless powder (5.7% water per analysis).

Analysis: C 35.11 H 4.58 N 11.37 S 5.21 Gd 25.54 (Calcd.) C 35.04 H 4.64 N 11.31 S 5.15 Gd 25.48 (Found)

EXAMPLE 2

(a) 1-Dibenzylamino-5,6-epoxy-3-oxahexane 100 g (414 mmol) of N-dibenzylaminoethanol is dissolved in 200 ml of methylene chloride and added dropwise at 0° C. to a vigorously stirred mixture of 250 ml 50% sodium hydroxide solution, 7.03 g (20.7 mmol) of tetra-n-butylammonium bisulfate, 153.4 g (1.657 mol) of epichlorohydrin. The mixture is stirred for 8 hours at 0° C., overnight at room temperature, then diluted with 2 l of water and extracted three times with 500 ml of methylene chloride. The combined organic phases are dried over magnesium sulfate and evaporated under vacuum. The oil that remains is subjected to flash chromatography (silica gel/mobile phase:methylene chloride/hexane/acetone 20/10/3). Yield: 96.12 g (78% of theory) of a colorless oil.

Analysis: C 76.74 H 7.79 N 4.71 (Calcd.) C 76.68 H 7.85 N 4.66 (Found)

(b) 10-(6-Dibenzylamino-2-hydroxy-4-oxahexyl)-1,4,7-triscarboxymethyl-1,4,7,10-tetraazacyclododecane 34.34 g (115.47 mmol) of the title compound of Example 2(a) and 20 g (57.74 mmol) of 1,4,7-triscarboxymethyl-1,4,7,10-tetraazacyclododecane (= DO3A) are dissolved in a mixture of 60 ml of dioxane/350 ml of water, and the pH is set at 10 with 6N potassium hydroxide solution. The mixture is stirred for 24 hours at 40° C. and worked up as described in Example 1(b). Yield: 26.39 g (71% of theory based on DO3A) of a vitreous solid (7.1% water per analysis).

Analysis: C 61.57 H 7.67 N 10.88 (Calcd.) C 61.49 H 7.80 N 10.79 (Found)

(c) Gadolinium Complex of 10-(6-Dibenzylamino-2-hydroxy-4-oxahexyl)-1,4,7-triscarboxymethyl-1,4,7,10-tetraazacyclododecane 23 g (35.73 mmol) of the title compound of Example 2(b) is dissolved in a solution of 150 ml of deionized water/50 ml of methanol, and 6.48 g (17.86 mmol) of gadolinium oxide is added. The mixture is refluxed for 2 hours, 3 g of active carbon is added, and refluxing is performed for another hour. The solution is filtered in the hot state and the filtrate evaporated to dryness under vacuum, thus obtaining 27.65 g (97% of theory) of the title compound as a vitreous solid (7.8% water per analysis).

Analysis: C 49.67 H 5.81 N 8.78 Gd 19.71 (Calcd.) C 49.61 H 5.89 N 8.71 Gd 19.61 (Found)

(d) Gadolinium Complex of 10-(6-Amino-2-hydroxy-4-oxahexyl)-1,4,7-triscarboxymethyl-1,4,7,10-tetraazacyclododecane 25 g (31.33 mmol) of the title compound of Example 2(c) is dissolved in a mixture of 250 ml of deionized water/150 ml of methanol, and 10 g of palladium catalyst (10% Pd on active carbon) is added. The mixture is then hydrogenated for 24 hours at 50° C. The product is filtered off from the catalyst and the filtrate evaporated under vacuum. Yield: 19.16 g (99% of theory) of the title compound as a vitreous solid (5.7% water per analysis).

Analysis: C 36.94 H 5.55 N 11.34 Gd 25.45 (Calcd.) C 36.88 H 5.59 N 11.27 Gd 25.38 (Found)

(e) Gadolinium Complex of 10-(6-Isothiocyanato-2-hydroxy-4-oxahexyl)-1,4,7-triscarboxymethyl-1,4,7,10-tetraazacyclododecane A solution of 5.58 g (48.56 mmol) of thiophosgene in 100 ml of chloroform is added to a solution of 15 g (24.28 mmol) of the title compound of Example 2(d) in 500 ml of deionized water and 20 ml of polyvinylpyridine (Reillex). The two-phase solution is stirred for 10 minutes at 40° C., then for one hour at room temperature, and filtered. The organic phase is separated and the aqueous phase extracted twice with 200 ml of chloroform. Then the aqueous phase is freeze-dried. Yield: 15.7 g (98% of theory) of a colorless powder (6.1% water per analysis).

Analysis: C 36.41 H 4.89 N 10.61 Gd 23.83 S 4.86 (Calcd.) C 36.35 H 4.95 N 10.51 Gd 23.71 S 4.78 (Found)

EXAMPLE 3

Gadolinium Complex of 10-(9-Bromo-2-hydroxy-8-oxo-4-oxa-7-azanonyl)-1,4,7-triscarboxymethyl-1,4,7,10-tetraazacyclododecane 10 g (16.19 mmol) of the title compound of Example 2(e) is dissolved in 50 ml of water and brought to pH 9 with 3N sodium hydroxide solution. At 0° C., a solution of 4.25 g (21.04 mmol) of bromoacetyl bromide in 20 ml of dioxane is added dropwise thereto, and the pH is maintained at pH 9 by addition of 3N sodium hydroxide solution. The mixture is stirred for one hour at 0° C., for two hours at room temperature, then evaporated under vacuum and the residue chromatographed ("Li-Chroprep RP-18" Merck/mobile phase: acetonitrile/H$_2$O gradient). After evaporation of the main fractions under vacuum, 10.64 g (89% of theory) of the title compound is obtained as a crystalline solid (5.4% water per analysis).

Analysis: C 34.15 H 4.78 N 9.48 Gd 21.29 Br 10.82 (Calcd.) C 34.11 H 4.85 N 9.41 Gd 21.19 Br 10.75 (Found)

EXAMPLE 4

(a) 1-Dibenzylamino-5-hydroxy-3-oxapentane

A mixture of 50 g (475.56 mmol) of 2-(2-aminoethoxy) ethanol and 144.6 g (1.046 mol) of potassium carbonate in 600 ml of EtOH/60 ml of water is heated to 60° C. To this mixture is added dropwise within one hour 178.95 g (1.046 mol) of benzyl bromide and then the mixture is refluxed for 2 hours, evaporated under vacuum, the residue taken up with 1 liter of methylene chloride, and filtered off from the salts. The filtrate is concentrated under vacuum and purified by flash chromatography (silica gel/mobile phase: methylene chloride/hexane/acetone:10/5/1). Yield: 127.58 g (94% of theory) of a colorless oil.

Analysis: C 75.76 H 8.12 N 4.91 (Calcd.) C 75.71 H 8.18 N 4.85 (Found)

(b) 1-Dibenzylamino-8,9-epoxy-3,6-dioxanonane

At 0° C., a solution of 125 g (438 mmol) of the title compound of Example 4(a) in 200 ml of methylene chloride is added dropwise to a thoroughly stirred suspension of 162.11 g (1.752 mol) of epichlorohydrin, 8.2 g (24.15 mmol) of tetra-n-butylammonium bisulfate, and 250 ml of 50% sodium hydroxide solution. The mixture is stirred for 8 hours at 0° C., overnight at room temperature. The mixture is diluted with 2 l of water and extracted twice with 500 ml of methylene chloride. The combined organic phases are dried over magnesium sulfate and evaporated under vacuum. The remaining oil is purified by flash chromatography (silica gel/mobile phase: methylene chloride/hexane/acetone:20/10/3). Yield: 116.5 g (78% of theory) of a colorless oil.

Analysis: C 73.87 H 7.79 N 4.10 (Calcd.) C 73.78 H 7.95 N 4.03 (Found)

(c) 10-(9-Dibenzylamino-2-hydroxy-4,7-dioxanonyl)-1,4,7-triscarboxymethyl-1,4,7,10-tetraazacyclododecane 39.43 g (115.47 mmol) of the title compound of Example 4(b) and 20 g (57.74 mmol) of 1,4,7-triscarboxymethyl-1,4,7,10-tetraazacyclododecane ($\hat{=}$ DO3A) are dissolved in a mixture of 60 ml of dioxane/250 ml of water, and the pH is adjusted to 10 with 6N potassium hydroxide solution. The mixture is stirred for 24 hours at 40° C. and then worked up as described in Example 1(b). Yield: 28.59 g (72% of theory based on DO3A) of a vitreous solid (6.3% water per analysis).

Analysis: C 61.12 H 7.77 N 10.18 (Calcd.) C 61.07 H 7.84 N 10.05 (Found)

(d) Gadolinium Complex of 10-(9-Dibenzylamino-2-hydroxy-4,7-dioxanonyl)-1,4,7-triscarboxymethyl-1,4,7,10-tetraazacyclododecane 25 g (36.35 mmol) of the title compound of Example 4(c) is dissolved in a solution of 150 ml of deionized water/50 ml of methanol, and 6.59 g (18.17 mmol) of gadolinium oxide is added thereto. The mixture is refluxed for 2 hours, 3 g of active carbon is added, and the mixture is refluxed for another hour. The solution is filtered in the hot state and the filtrate evaporated to dryness under vacuum. Yield: 30.0 g (98% of theory) of the title compound as a vitreous solid (5.4% water per analysis).

Analysis: C 49.92 H 5.98 N 8.32 Gd 18.67 (Calcd.) C 49.83 H 5.90 N 8.34 Gd 18.58 (Found)

Analogously, the corresponding europium complex is obtained with Eu, $^{151}Eu_2O_3$.

Analysis: C 50.24 H 6.02 N 8.37 Eu 18.16 (Calcd.) C 50.17 H 5.96 N 8.29 Eu 18.09 (Found)

(e) Gadolinium Complex of 10-(9-Amino-2-hydroxy-4,7-dioxanonyl)-1,4,7-triscarboxymethyl-1,4,7,10-tetraazacyclododecane 29 g (34.44 mmol) of the title compound of Example 4(d) is dissolved in a mixture of 250 ml of deionized water/150 ml methanol, and 10 g of palladium catalyst (10% Pd on active carbon) is added thereto. Then the mixture is hydrogenated for 24 hours at 50° C., filtered off from the catalyst, and the filtrate is evaporated under vacuum. Yield: 22.56 g (99% of theory) of the title compound as a vitreous solid (6.5% water per analysis).

Analysis: C 38.11 H 5.79 N 10.58 Gd 23.76 (Calcd.) C 38.05 H 5.86 N 10.47 Gd 23.65 (Found)

(f) Gadolinium Complex of 10-(9-Isothiocyanato-2-hydroxy-4,7-dioxanonyl)-1,4,7-triscarboxymethyl-1,4,7,10-tetraazacyclododecane A solution of 5.21 g (45.33 mmol) of thiophosgene in 100 ml of chloroform is added to a solution of 15 g (22.66 mmol) of the title compound of Example 4(e) in 500 ml of deionized water and 20 ml of polyvinylpyridine (Reillex). The two-phase solution is stirred for 10 minutes at 40° C., then for one hour at room temperature, and filtered. The organic phase is separated and the aqueous phase is extracted twice with 200 ml of chloroform. Subsequently the aqueous phase is freeze-dried. Yield: 15.64 g (98% of theory) of a colorless powder (5.9% water per analysis).

Analysis: C 37.54 H 5.15 N 9.95 Gd 22.34 S 4.55 (Calcd.) C 37.49 H 5.11 N 9.91 Gd 22.27 S 4.61 (Found)

EXAMPLE 5

(a) 3,6,9-Tris(p-tolylsulfonyl)-3,6,9,15-tetraazabicyclo[9.3.1]pentadeca-1(15),11,13-triene At 100° C., a solution of 35.2 g (200 mol) of 2,6-bis(chloromethyl)pyridine (dissolved in 700 ml of dimethylformamide) is added dropwise within 3 hours to 121.9 g (200 mol) of N,N',N"-tris(p-tolylsulfonyl)-diethylenetriamine-N,N"-disodium salt in 1600 ml of dimethylformamide. The mixture is agitated overnight at 100° C. Two liters of water is dripped into the hot solution, and the latter is allowed to cool down to 0° C. The precipitate is suctioned off and washed with water. After drying under vacuum (60° C.), the product is recrystallized from acetonitrile, thus obtaining 92.3 g (69% of theory) of the title compound as a colorless powder.

Analysis: C 57.46 H 5.43 N 8.38 S 14.38 (Calcd.) C 57.39 H 5.48 N 8.35 S 14.35 (Found)

(b) 3,6,9,15-Tetraazabicyclo[9.3.1]pentadeca-1(15),11,13-triene Tetrahydrosulfate 90.3 g (135 mmol) of the title compound of Example 5(a) is introduced into 270 ml of concentrated sulfuric acid and stirred for 48 hours at 100° C. The mixture is cooled to 0° C., and 1.35 l of absolute ether is added dropwise thereto. The precipitate is suctioned off and extracted by stirring in 800 ml of methanol. After filtration and concentration, the product is dried under vacuum at 50° C. Yield: 42.6 g (52.7% of theory) of a solid which deliquesces in the open air.

Analysis: C 22.07 H 4.38 N 9.36 S 21.43 (Calcd.) C 22.10 H 4.42 N 9.31 S 21.40 (Found)

(c) 3,6,9,15-Tetraazabicyclo[9.3.1]pentadeca-1(15),11,13-triene 40.0 g (66.8 mmol) of the title compound of Example 5(b) is dissolved in 100 ml of water and adjusted to pH 11 with 32% strength sodium hydroxide solution. The mixture is extracted 8 times with 150 ml of methylene chloride and dried over magnesium sulfate. After evaporation under vacuum, 9.79 g (71% of theory) of a yellowish powder is obtained.

Analysis: C 64.04 H 8.79 N 27.16 (Calcd.) C 63.91 H 8.85 N 26.98 (Found)

(d) 3,6,9-Tris(acetyl)-3,6,9,15-tetraazabicyclo[9.3.1]-pentadeca-1(15),11,13-triene 15.8 g (76.6 mmol) of the title compound of Example 5(c), 42.7 ml of triethylamine (306.4 mmol) and 50 mg of dimethylaminopyridine (DMAP) are dissolved in 300 ml of absolute methylene chloride. The mixture is combined with 28.9 ml (306.4 mmol) of acetic anhydride and stirred overnight at room temperature. The solvent is evaporated under vacuum, and the residue is taken up in 200 ml of 3% sodium carbonate solution. The mixture is extracted twice with 150 ml of methylene chloride. After drying the organic phase over magnesium sulfate, the mixture is evaporated under vacuum. The residue is recrystallized from ether/ethyl acetate, thus obtaining 23.93 g (94% of theory) of the title compound as white flakes.

Analysis: C 61.42 H 7.28 N 16.86 (Calcd.) C 61.48 H 7.37 N 16.80 (Found)

(e) 3,6,9-Tris(acetyl)-3,6,9,15-tetraazabicyclo[9.3-1]-pentadeca-1(15),11,13-triene-15-N-oxide 22.5 g (67.7 mmol) of the title compound of Example 5(d) is dissolved in 100 ml of glacial acetic acid. To this solution is added 7.7 ml of a 30% strength hydrogen peroxide solution, and the mixture is heated for 4 hours to 70° C. Then another 3.9 ml of 30% strength hydrogen peroxide solution is added, and the mixture is stirred for another hour at 70° C. The mixture is then concentrated to one-third under vacuum, and gently combined with saturated sodium carbonate solution until an alkaline reaction is obtained. The mixture is extracted twice with 250 ml of methylene chloride and the organic phases are then dried over magnesium sulfate. Evaporation under vacuum and crystallization from ether/ethyl acetate yield 18.63 g (79% of theory) of the title compound as a crystalline powder.

Analysis: C 58.60 H 6.94 N 16.08 (Calcd.) C 58.47 H 6.88 N 16.14 (Found)

(f) 13-Nitro-3,6,9-tris(acetyl)-3,6,9,15-tetraazabicyclo[9.3.1]pentadeca-1(15),11,13-triene-15-N-oxide 17 g (48.8 mmol) of the title compound of Example 5(e) is dissolved in 40 ml of 90% sulfuric acid and heated to 60° C. To this solution is added dropwise 14 ml of concentrated nitric acid (d=1.36), and the mixture is stirred for 3 hours at 60° C. The mixture is poured on ice, the precipitate is filtered and washed with a large amount of water. After drying under vacuum, an orange-colored powder is obtained which is recrystallized from acetone. Yield: 9.2 g (48% of theory) of yellow rhombi.

Analysis: C 51.90 H 5.89 N 17.80 (Calcd.) C 52.01 H 5.76 N 17.46 (Found)

(g) 13-Chloro-3,6,9-tris(acetyl)-3,6,9,15-tetraazabicyclo[9.3.1]pentadeca-1(15),11,13-triene-15-N-oxide 7.3 g (18.56 mmol) of the title compound of Example 5(f) is heated in 50 ml of acetyl chloride for 4 hours to 50° C. The mixture is concentrated under vacuum and the residue taken up in 200 ml of 3% strength sodium carbonate solution. The mixture is extracted three times with 100 ml of chloroform and dried over magnesium sulfate. After removal of the solvent under vacuum, the product is recrystallized from ether/ethyl acetate. Yield: 6.18 g (87% of theory) of a colorless crystalline powder.

Analysis: C 53.33 H 6.05 N 14.64 Cl 9.26 (Calcd.) C 53.48 H 5.98 N 14.71 Cl 9.20 (Found)

(h) 13-Chloro-3,6,9-tris(acetyl)-3,6,9,15-tetraazabicyclo[9.3.1]pentadeca-1(15),11,13-triene 6.0 g (15.67 mmol) of the title compound of Example 5(g) is dissolved in 300 ml of ethanol, 1 ml of concentrated hydrochloric acid is added thereto, and the mixture is hydrogenated over Pd/C. After hydrogen absorption has ceased, the mixture is filtered off from the catalyst and evaporated under vacuum. The residue is taken up in 100 ml of 3% strength sodium carbonate solution and extracted twice with 100 ml of chloroform. The organic phases are dried over magnesium sulfate and evaporated under vacuum. Crystallization of the residue from ether/ethyl acetate yields 5.34 g (93% of theory) of the title compound as a colorless powder.

Analysis: C 55.66 H 6.32 N 15.27 Cl 9.66 (Calcd.) C 55.57 H 6.38 N 15.31 Cl 9.59 (Found)

(i) 13-Chloro-3,6,9,15-tetraazabicyclo[9.3.1]pentadeca-1(15),11,13-triene 5.1 g (13.9 mmol) of the title compound of Example 5(h) is dissolved under nitrogen in 50 ml of dioxane. To this mixture is added 6.24 g (55.6 mmol) of potassium tert-butylate, and the mixture is refluxed overnight, evaporated to dryness, taken up in 50 ml of water, and extracted 4 times with 100 ml of hot toluene. The combined toluene phases are dried over magnesium sulfate and evaporated under vacuum. The residue is purified by chromatography (silica gel/methanol/water/ammonia (aq. 33%)=10/1/1). Yield: 3.01 g (90% of theory) of a slightly yellowish oil which crystallizes after a short time.

Analysis: C 54.88 H 7.12 N 23.28 Cl 14.73 (Calcd.) C 54.93 H 7.06 N 23.41 Cl 14.81 (Found)

(k) 13-Chloro-3,6,9-tris(tert-butoxycarbonylmethyl)-3,6,9,15-tetraazabicyclo[9.3.1]pentadeca-1(15),11,13-triene 18.72 g (95.96 mmol) of bromoacetic acid tert-butyl ester is added to 7 g (29.08 mmol) of the title compound of Example 5(i) and 10.17 g (95.96 mmol) of sodium carbonate in 200 ml of acetonitrile, and the mixture is stirred at room temperature for 24 hours.

The mixture is evaporated under vacuum, the residue is taken up in 300 ml of water and extracted three times with 200 ml of methylene chloride. After drying of the organic phases over magnesium sulfate, the mixture is concentrated under vacuum and the remaining oil is chromatographed on silica gel (mobile phase: methylene chloride/ethanol=15/1). Yield: 14.08 g (83% of theory) of a colorless oil.

Analysis: C 59.73 H 8.12 N 9.61 Cl 6.08 (Calcd.) C 59.67 H 8.25 N 9.58 Cl 6.01 (Found)

(l) 13-Azido-3,6,9-tris(tert-butoxycarbonylmethyl)-3,6,9,15-tetraazabicyclo[9.3.1]pentadeca-1(15),11,13-triene 21 g (36.01 mmol) of the title compound of Example 5(k) is dissolved in 200 ml of dimethylformamide, and 7.02 g (108 mmol) of sodium azide as well as 951 mg (3.6 mmol) of 18-crown-6 are added thereto. The mixture is stirred for 48 hours at 90° C. After cooling to room temperature, the mixture is poured into 1.5 l of ice water and extracted three times with 200 ml of ethyl acetate. After drying the organic phase over magnesium sulfate, the mixture is evaporated and the remaining oil is chromatographed on silica gel (mobile phase: methylene chloride/ethanol=15/1). Yield: 10.83 g (51% of theory) of a pale-yellow oil.

Analysis: C 59.06 H 8.03 N 16.63 (Calcd.) C 59.17 H 8.05 N 16.51 (Found)

(m) 13-Amino-3,6,9-tris(tert-butoxycarbonylmethyl)-3,6,9,15-tetraazabicyclo[9.3.1]pentadeca-1(15),11,13-triene 10 g (16.96 mmol) of the title compound of Example 5(l) is dissolved in 400 ml of ethanol, and 1 g of Pearlman catalyst (20% palladium hydroxide on carbon) is added thereto. After 24 hours of hydrogenation under normal pressure, the product is suctioned off from the catalyst and evaporated under vacuum. The remaining oil is chromatographed on silica gel (mobile phase: methylene chloride/methanol/triethylamine=10/1/0.05), thus obtaining 8.89 g (93% of theory) of a slightly yellowish oil.

Analysis: C 61.78 H 8.76 N 12.42 (Calcd.) C 61.67 H 8.91 N 12.35 (Found)

(n) 13-Amino-3,6,9-tris(carboxymethyl)-3,6,9,15-tetraazabicycl[9.3.1]pentadeca-1(15),11,13-triene 8.2 g (14.55 mmol) of the title compound of Example 5(m) is dissolved in 100 ml of trifluoroacetic acid and stirred for 6 hours at room temperature. After removal of the solvent by evaporation under vacuum, the residue is dissolved in 100 ml of water and passed over a column filled with poly(4-vinyl-pyridine). After evaporation under vacuum and crystallization from methanol/acetone, 5.24 g (91% of theory) of a strongly hygroscopic solid is obtained.

Analysis: C 51.64 H 6.37 N 17.71 (Calcd.) C 51.74 H 6.31 N 17.63 (Found)

(o) Gadolinium Complex of 13-Amino-3,6,9-tris (carboxymethyl)-3,6,9,15-tetraazabicyclo[9.3.1]pentadeca-1(15),11,13-triene 4.8 g (12.14 mmol) of the title compound of Example 5(n) is dissolved in 35 ml of deionized water, and 2.2 g (6.07 mmol) of gadolinium oxide is added. The mixture is stirred for 3 hours at 90° C., maintaining the pH by adding acetic acid at 5.5. The solution is filtered and passed over a column filled with poly(4-vinylpyridine). After treatment with active carbon, the mixture is again filtered and freeze-dried. Yield: 6.07 g (91% of theory) of an amorphous powder which, per analysis, contains 12.1% water.

Analysis: C 37.15 H 4.06 N 12.74 Gd 28.61 (Calcd.) C 37.08 H 4.17 N 12.68 Gd 28.54 (Found)

(p) Gadolinium Complex of 13-Isothiocyanato-3,6,9-tris (carboxymethyl)-3,6,9,15-tetraazabicyclo-[9.3.1]pentadeca-1(15),11,13-triene 5.49 g (10 mmol) of the title compound of Example 5(o) and 10 ml of polyvinylpyridine (Reillex) are dissolved in 100 ml of deionized water, and 3.45 g (30 mmol) of thiophosgene in 50 ml of chloroform is added thereto. The mixture is stirred for 10 minutes at 40° C., then for one hour at room temperature, and filtered. The organic phase is separated, and the aqueous phase is extracted twice with 50 ml of chloroform. Then the product is freeze-dried. Yield: 5.8 g (98% of theory) of a white powder (7.9% water per analysis).

Analysis: C 36.54 H 3.41 N 11.84 Gd 26.58 S 5.43 (Calcd.) C 36.49 H 3.48 N 11.81 Gd 26.47 S 5.32 (Found)

EXAMPLE 6

(a) Hexamethyl Ester of the Tris(aminoethyl)amine Cascade Polymer 7.6 ml of tris(aminoethyl)amine (50 mmol) is dissolved in 10 ml of methanol and added dropwise to 54.5 ml (600 mmol) of methyl acrylate. The mixture is stirred for 3 days at room temperature and then evaporated under vacuum. The remaining oil is precipitated from methanol/ether/hexane. Yield: 30.59 g (92.3% of theory) of a slightly yellowish oil.

Analysis: C 54.37 H 8.21 N 8.45 (Calcd.) C 54.32 H 8.29 N 8.43 (Found)

(b) Hexaamine of the Tris (aminoethyl) amine Cascade Polymer 26.5 g of the hexamethyl ester described in Example 6(a) (40 mmol) is dissolved in 20 ml of methanol and gradually added dropwise to 242 ml of ethylenediamine (3.6 mol) and then stirred for 3 days at room temperature. The solution is evaporated under vacuum, and the remaining oil is reprecipitated from methanol/ether. Yield: 31.25 g (94% of theory) of an oil having a slightly yellow color.

Analysis: C 52.03 H 9.46 N 26.96 (Calcd.) C 51.97 H 9.49 N 26.89 (Found)

(c) Dodecamethyl Ester of the Tris(aminoethyl)amine Cascade Polymer 30.1 g (36.2 mmol) of the hexaamine described in Example 6(b) in 50 ml of methanol is added dropwise to 103 ml (1.14 mol) of methyl acrylate so slowly that the solution remains clear, and the latter is stirred for 5 days at room temperature. After concentration under vacuum, the mixture is repeatedly precipitated from methanol/ether/hexane. Yield: 64.2 g (95.1%) of a yellowish oil.

The M+H$^+$ peak is clearly recognizable in the FAB mass spectrum. An analytical sample showed the elementary analysis set forth below after correction of methanol, determined by gas chromatography:

C 54.12 H 8.11 N 12.02 (Calcd.) C 54.01 H 8.19 N 11.98 (Found)

(d) Dodecaamine of the Tris(aminoethyl)amine Cascade Polymer 64.0 g (34.3 mmol) of the dodecamethyl ester described in Example 6(c) is dissolved in 50 ml of methanol and gradually added dropwise to 870 ml of ethylenediamine (13 mol), and stirred for 5 days at room temperature. After concentration under vacuum, the mixture is repeatedly precipitated from methanol/ether until no ethylenediamine can be detected any more by thin-layer chromatography. Yield: 73.7 g (97%) of a viscous, yellowish oil. The quasi molecule peak is clearly recognizable at 2201 in the FAB mass spectrum. An analytical sample showed the following elementary analysis after correction of methanol determined by gas chromatography:

C 52.39 H 9.07 N 25.46 (Calcd.) C 52.29 H 9.21 N 25.71 (Found)

(e) 24-Methyl Ester of the Tris(aminoethyl)amine Cascade Polymer 68.0 g (30 mmol) of the 12-amine (Example 6d) is dissolved in 120 ml of methanol and added dropwise to 270 ml (3 mol) of methyl acrylate so gradually that the solution remains homogeneous (addition within 3 hours). After 5 days, the mixture is worked up analogously to Example 6(c). Yield: 119.7 g (93.5%) of a yellowish oil. The FAB mass spectrum shows the quasi molecule ion at m/e=4268. An analytical sample showed the following elementary analysis after correction of methanol determined by gas chromatography:

C 54.04 H 8.08 N 13.13 (Calcd.) C 54.28 H 8.01 N 12.99 (Found)

(f) 24-Amine of the Tris(aminoethyl)amine Cascade Polymer 39.87 g (9.3 mmol) of the 24-methyl ester is dissolved in 100 ml of methanol and added dropwise to 1.5 l of ethylenediamine (23 mol), and worked up after 7 days analogously to Example 6(d), thus obtaining 44.0 g (95.9%) of a viscous yellow-colored oil. The compound is uniform in the-HPLC chromatogram in 1-molar NaClO$_4$ in "Lichrospher" DIOL 100, 500, 1000 (Merck).

Analysis: C 52.51 H 8.94 N 24.95 (Calcd.) C 52.17 H 8.72 N 25.27 (Found)

(g) [10-Carboxy-3,6-bis(carboxymethyl)-9-ethoxy-carbonylmethyl-3,6,9-triazadecanoyl] Derivative of the 24-Amine of the Tris(aminoethyl)amine Cascade Polymer 4.94 g (1 mmol) of the aforedescribed 24-amine (Example 6f) is dissolved in 300 ml of H$_2$O. Within 2 hours, 29.04 g (72 mmol) of N$^3$-(2,6-dioxomorpholinoethyl)-N$^6$-(ethoxycarbonylmethyl)-3,6-diazaoctanedioic acid (Example 13a of EP 0,331,616) is then added in portions in the solid form, the pH being maintained at 9.0 by adding 1N NaOH. The mixture is then stirred for 30 minutes, adjusted to pH 7 with "Amberlite" IR 120 (H⁺ form), and suctioned off from the ion exchanger. The solution is subjected to ultrafiltration ("AMICON" YM5 membrane), and thereafter freeze-dried. Yield: 13.6 g of a colorless, flaky powder. $H_2O$ content (Karl-Fischer):3.4%.

100 mg of the anhydrous complexing compound turn 24 mg $Gd^{3+}$ into a complex (indicator xylenol orange) (occupation value with DTPA>92%).

(h) Gd Complex of [10-Carboxy-3,6-bis(carboxymethyl)-9-ethoxycarbonylmethyl-3,6,9-triazadecanoyl] Derivative of the 24-Amine of the Tris(aminoethyl)-amine Cascade Polymer 10.0 g of the complexing compound described in Example 6(g) is dissolved in 500 ml of $H_2O$ and combined with 2.77 g of $Gd_2O_3$ (≙2.40 g Gd), stirred for 30 minutes at 80° C., adjusted, after cooling, to pH 7 with ion exchanger, membrane-filtered, and freeze-dried.
Yield: 12.1 g of a colorless, flaky lyophilized product.
$H_2O$ content: 5.6%
Gd analysis (AAS): 17.9%
$T_1$ relaxation ($H_2O$): 12.98±0.27 [1/mmol·sec](plasma): 13.23±0.35 [1/mmol·sec]

EXAMPLE 7

(a) 48-Methyl Ester of the Tris(aminoethyl)amine Cascade Polymer 19.8 g (4 mmol) of the 24-amine described in Example 6(f) is dissolved in 100 ml of methanol and added dropwise within 5 hours to 200 ml (2.2 mol) of methyl acrylate at 50° C., and stirred for 3 days at this temperature. After repeated precipitation from methanol/ether/hexane, 34.4 g (95%) of a viscous oil is obtained.

Analysis: C 54.01 H 8.07 N 13.59 (Calcd. C 53.52 H 8.19 N 13.23 (Found)

(b) 48-Amine of the Tris(aminoethyl)amine Cascade Polymer 23.2 g (2.5 mmol) of the 48-ester obtained in the preceding Example 7(a) is dissolved in 75 ml of methanol and added dropwise to 1000 ml (15 mol) of ethylenediamine, and worked up after 7 days in analogy to Example 6(d). Yield: 25.0 g (96%) of a viscous oil. The oil is uniform as per HPLC in 1-molar $NaClO_4$ on "Lichrospher" DIOL-100, 500, 1000 (Merck). Titration of an analytical sample with 1N HCl yields 96.4% of theory.

(c) [10-Carboxy-3,6-bis(carboxymethyl)-9-ethoxycarbonylmethyl-3,6,9-triazadecanoyl] Derivative of the 48-Amine of the Tris(amino-ethyl)amine Cascade Polymer 5.21 g (0.5 mmol) of the 48-amine described in Example 7(b) is dissolved in 300 ml of $H_2O$. Within 2 hours, 29.04 g (72 mmol) of $N^3$-(2,6-dioxomorpholinoethyl)-$N^6$-(ethoxycarbonylmethyl)-3,6-diazaoctanedioic acid (Example 13a of EP 0,331,616) is added to this solution in portions in the solid form. The pH is maintained at 9.0 by the simultaneous addition of 1N NaOH. The mixture is worked up analogously to Example 6(g).
Yield: 13.3 g of a colorless lyophilized product.
$H_2O$ content (Karl-Fischer): 4.7%
100 mg of the polymer complexes 24 mg of $Gd^{3+}$.

(d) Gd Complex of the [10-Carboxy-3,6-bis(carboxymethyl)-9-ethoxycarbonylmethyl-3,6,9-triazadecanoyl] Derivative of the 48-Amine of the Tris(aminoethyl)amine Cascade Polymer 10.0 g of the complexing compound described in Example 7(c) is dissolved in 500 ml of $H_2O$ and combined with 2.77 g of $Gd_2O_3$ (≙2.40 g Gd), stirred for 30 minutes at 80° C., and worked up analogously to Example 6(h).
Yield: 12.2 g of a colorless flaky powder.

$H_2O$ content: 3.9%
Gd analysis (AAS): 17.8%
$T_1$ relaxation ($H_2O$): 13.52±0.37 [1/mmol·sec](plasma): 13.35±0.31 [1/mmol·sec]

EXAMPLE 8

Gd Complex of the [10-Carboxy-3,6,9-tris(carboxymethyl)-3,6,9-triazadecanoyl] Derivative of the 48-Amine of the Tris(aminoethyl)amine Cascade Polymer 10.42 g (0.35 mmol) of the 48-DTPA ethyl ester disclosed in Example 7(c) is dissolved in 100 ml of 2N NaOH and stirred for 4 hours at room temperature. The alkaline solution is adjusted to pH 4 with "Amberlite" IR 120 (H⁺ form), suctioned off from the ion exchanger, and combined with 2.88 g of $Gd_2O_3$ (≙2.50 g Gd), stirred for 30 minutes at 80° C., adjusted to pH 7.2 with 1N NaOH, and the thus-produced solution is subjected to ultra-filtration ("AMICON" YM5 membrane). The desalted solution is finally freeze-dried, thus obtaining 12.1 g of a colorless powder.
$H_2O$ content (Karl-Fischer): 4.3%
Gd analysis (AAS): 19.17%
Melting point: 230° C. (onset of discoloration)
$T_1$ relaxation ($H_2O$): 13.11±0.33 [1/mmol·sec](plasma): 13.09±0.27 ]1/mmol·sec]
Osmolality (0.5 mol/l at 37° C.): 0.46 [osmol/kg]
Comparison "Magnevist": 1.96 [osmol/kg]
$LD_{50}$ (i.v. in mice): 30 mmol/kg
Comparison "Magnevist": ≦10 mmol/kg

EXAMPLE 9

(a) Pentamethyl Ester of the Diethylenetriamine Cascade Polymer 5.54 ml of diethylenetriamine (50 mmol) is dissolved in 20 ml of methanol and added dropwise to 45.4 ml of methyl acrylate (500 mmol). The mixture is stirred for 5 days at room temperature and then evaporated under vacuum. The remaining oil is reprecipitated from methanol/ether/hexane. Yield: 24.8 g (92.9%) of a slightly yellowish oil.

Analysis: C 54.02 H 8.12 N 7.87 (Calcd.) C 53.92 H 8.06 N 7.92 (Found)

(b) Pentaamine of the Diethylenetriamine Cascade Polymer 21.3 g of the pentamethyl ester described in Example 9(a) (40 mmol) is dissolved in 20 ml of methanol and added dropwise slowly to 202 ml of ethylenediamine (3.0 mol) and then stirred for 3 days at room temperature. The solution is evaporated under vacuum and the remaining oil reprecipitated from methanol/ether. Yield: 24.8 g (92%) of a slightly yellow-colored oil.

Analysis: C 51.69 H 9.42 N 27.02 (Calcd.) C 51.48 H 9.36 N 27.15 (Found)

(c) Decamethyl Ester of the Diethylenetriamine Cascade Polymer 20.7 g of the pentaamine described in Example 9(b) in 35 ml of methanol is added to 68 ml (0.75 mol) of methyl acrylate so gradually that the solution remains clear; the latter is stirred for 5 days at room temperature. After concentration under vacuum, the mixture is repeatedly precipitated from methanol/ether/hexane. Yield: 39.8 g (84%) of a yellowish oil. The M+H⁺ peak can be clearly recognized in the FAB mass spectrum. After correction of the methanol content determined by gas chromatography, an analytical sample showed the following elementary analysis:

C 54.00 H 8.08 N 11.86' (Calcd.) C 54.27 H 8.16 N 11.63 (Found)

(d) Decaamine of the Diethylenetriamine Cascade Polymer 39.5 g (25.7 mmol) of the decamethyl ester disclosed in Example 9(c) is dissolved in 30 ml of methanol and added gradually to 520 ml (7.8 mol) of ethylenediamine, and stirred for 5 days at room temperature. After concentration under vacuum, the mixture is repeatedly precipitated from methanol/ether until no ethylenediamine can be detected any longer by thin-layer chromatography. Yield: 44.9 g (96.2%) of a yellowish oil. The quasi molecule peak can be readily seen in the FAB mass spectrum at m/e=1815. After correction of the methanol content determined by gas chromatography, an analytical sample showed the following elementary analysis:

C 52.27 H 9.05 N 25.46 (Calcd.) C 52.11 H 9.09 N 25.67 (Found)

(e) 20-Methyl Ester of the Diethylenetriamine Cascade Polymer 41.8 g (23 mmol) of the decaamine (Example 9d) is dissolved in 100 ml of methanol and added dropwise to 200 ml (2.2 mol) of methyl acrylate so gradually that the solution remains homogeneous (2 hours). After 5 days, the mixture is worked up analogously to Example 9(c). Yield: 72.0 g (88.5%) of a yellowish oil. The FAB mass spectrum shows the quasi molecule at m/e=3536. After correction of the methanol content determined by gas chromatography, an analytical sample showed the following elementary analysis:

C 53.99 H 8.06 N 13.07 (Calcd.) C 53.71 H 8.14 N 13.10 (Found)

(f) 20-Amine of the Diethylenetriamine Cascade Polymer 68.7 g (19.4 mmol) of the 20-methyl ester is dissolved in 100 ml of methanol and added dropwise to 1.5 l (23 mol) of ethylenediamine, and worked up after 7 days analogously to Example 9(d), thus obtaining 74.3 g (93.5%) of a viscous oil. The oil is uniform in the HPLC in 1-molar $NaClO_4$ on "Lichrospher" DIOL-100, 500, 1000 (Merck). Titration of an analytical sample with 1N HCl yields 97.8% of theory.

Analysis: C 52.46 H 8.93 N 24.95 (Calcd.) C 51.98 H 8.99 N 24.49 (Found)

(g) 40-Methyl Ester of the Diethylenetriamine Cascade Polymer 20.5 g (5 mmol) of the 20-amine described in Example 9(f) is dissolved in 100 ml of methanol and added dropwise within 5 hours to 200 ml (2.2 mol) of methyl acrylate at 50° C.; the mixture is stirred for 3 days at this temperature. After repeated precipitation from methanol/ether/hexane, 34.3 g (91%) of a viscous oil is obtained.

Analysis: C 53.99 H 8.06 N 13.56 (Calcd.) C 53.69 H 8.12 N 13.21 (Found)

(h) 40-Amine of the Diethylenetriamine Cascade Polymer 26.4 g (3.5 mmol) of the 40-ester obtained in the preceding Example 9(g) is dissolved in 100 ml of methanol and added dropwise to 1,170 ml (17.5 mol) of ethylenediamine, and worked up after 7 days in analogy to Example 9(d). Yield: 28.7 g (94.6%) of a viscous, yellowish oil The oil is uniform as per HPLC in 1-molar $NaClO_4$ on "Lichrospher" DIOL-100, 500, 1000 (Merck). Titration of an analytical sample with 1N HCl yields 95.3% of theory.

Analysis: C 52.54 H 8.88 N 24.73 (Calcd.) C 52.73 H 8.57 N 24.35 (Found)

(i) Thioureido Conjugate of the Gd Complex of 10-(6-Isothiocyanato-2-hydroxy-4-oxahexyl)-1,4,7-triscarboxymethyl-1,4,7,10-tetraazacyclododecane with the 40-Amine of the Diethylenetriamine Cascade Polymer 2.17 g (0.25 mmol) of the 40-amine described in Example 9(h) is dissolved in 250 ml of $H_2O$. Under nitrogen, 8.43 g (12 mmol, 1.2-fold excess) of the isothiocyanate-Gd complex disclosed in Example 2(e) is added in the solid form in portions to this mixture, and the latter is stirred overnight at room temperature. After ultrafiltration ("AMICON" YM-10 membrane), the conductivity of the solution is set at a minimum by means of ion exchanger ("Amberlite" IR 120, $H^+$ form, and IRA 410, $OH^-$ form). The mixture is filtered off from the exchanger and freeze-dried.

Yield: 7.6 g (87%).
$H_2O$ content: 6.3%
Gd analysis (AAS): 15.6%
$T_1$ relaxation ($H_2O$): 12.43±0.51 [1/mmol·sec](plasma): 13.19±0.42 [1/mmol·sec]

Analysis (anhydrous): C 40.39 H 5.87 N 14.10 Gd 17.94 S 3.66 (Calcd.) C 40.67 H 6.15 N 13.88 Gd 16.88 S 3.47 (Found)

The following thioureido conjugates are obtained analogously:

from the isothiocyanate described in Example 1(e): C 39.65 H 5.70 N 14.85 S 3.85 Gd 18.89 (Calcd.) C 40.12 H 5.55 N 14.31 S 3.39 Gd 18.71 (Found)

from the isothiocyanate disclosed in Example 4(f): C 41.07 H 6.03 N 13.43 S 3.48 Gd 17.08 (Calcd.) C 40.69 H 5.97 N 13.57 S 3.61 Gd 16.88 (Found)

as well as, from the isothiocyanate described in Example 5(p): C 40.83 H 4.87 N 15.29 S 3.97 Gd 19.45 (Calcd.) C 40.67 H 5.01 N 15.24 S 3.70 Gd 19.11 (Found)

EXAMPLE 10

(a) Conjugate of the 48-Amine, Partially Occupied by Sebacic Acid Monohydrazide, of the Tris(aminoethyl)amine Cascade Polymer with $N^3$-(2,6-Dioxomorpholinoethyl)-$N^6$-(ethoxycarbonylmethyl)-3,6-diazaoctanedioic Acid 0.48 g (1.5 mmol) of sebacic acid mono-(N-tert-butoxycarbonyl)hydrazide (Example 58b of EP 0,331,616) is dissolved in tetrahydrofuran and combined, at −5° C., in succession with 4.16 ml (30 mmol) of triethylamine and 0.15 ml (1.58 mmol) of ethyl chloroformate. After 15 minutes, at −20° C., a solution of 6.51 g (30 mmol amino groups) of the 48-amine described in Example 7(b) in tetrahydrofuran/$H_2O$ (10:1) is added and the mixture is heated to room temperature. After 3 hours, tetrahydrofuran is distilled off, the mixture is diluted with $H_2O$ and combined, at pH 9, in portions with 36.3 g (90 mmol) of $N^3$-(2,6-dioxomorpholinoethyl)-$N^6$-(ethoxycarbonylmethyl)-3,6-diazaoctanedioic acid (Example 13a of EP 0,331,616), and then set to pH 7 with dilute HCl. The solution is filtered, the filtrate is purified by removing low-molecular components by way of an "AMICON" ultrafiltration membrane YM 10, and is finally freeze-dried. No impurities can be detected by thin-layer charomatography. Yield: 16.2 g The thus-obtained polymeric boc-hydrazide is taken up without further purification in trifluoroacetic acid, stirred for one hour at room temperature, and then precipitated with ether, suctioned off, and dried. The residue is set at pH 7.2 in $H_2O$ and freeze-dried.

Yield: 14.7 g

Hydrazide content: 1.9 mol-%, $H_2O$ content: 8.3% One gram of this compound complexes 192 mg of $Gd^{3+}$.

(b) Gd Complex of the Conjugate of the 48-Amine, Partially Occupied by Sebacic Acid Monohydrazide, of the Tris (aminoethyl)amine Cascade Polymer with $N^3$-(2,6-Dioxomorpholinoethyl)-$N^6$-(ethoxycarbonylmethyl)-3,6-diazaoctanedioic Acid 10.0 g of the complexing compound described in Example 10(a) is dissolved in 500 ml of $H_2O$, combined with 2.21 g of $Gd_2O_3$ (=1.92 g $Gd^{3+}$), and stirred for one hour at 80° C. The resultant solution is subjected to ultrafiltration and then freeze-dried.

Yield: 11.7 g of a colorless powder.
Gd content (AAS): 15.8%

Hydrazide content (by colorimetry): 1.8 mol-%
Melting point: 258° C. (onset of discoloration)
T₁ relaxation (H₂O): 12.23±0.41 [1/mmol·sec](plasma): 11.87±0.31 [1/mmol·sec]

EXAMPLE 11

Gd Complex of the [10-Carboxy-3,6,9-tris(carboxymethyl)-3,6,9-triazadecanoyl] Derivative of the 24-Amine of the Tris(aminoethyl)amine Cascade Polymer 7.29 g (0.5 mmol) of the 24-DTPA-ethyl ester described in Example 6(g) is dissolved in 70 ml of 2N NaOH and stirred for 4 hours at room temperature. The alkaline solution is adjusted to pH 4 with "Amberlite" IR 120 (H⁺ form), suctioned off from the ion exchanger, and combined with 2.11 g of $Gd_2O_3$ ($\hat{=}$1.83 g $Gd^{3+}$), stirred for 30 minutes at 80° C., adjusted to pH 7.2 with 1N NaOH, and the thus-produced solution is subjected to ultrafiltration. The desalted solution is finally freeze-dried, thus obtaining 8.51 g (96.4%) of a colorless powder.

H₂O content (Karl-Fischer): 3.9%
Gd analysis (AAS): 19.84%
Melting point: 250° C. (onset of discoloration)
T₁ relaxation (H₂O): 11.17±0.48 [1/mmol·sec](plasma): 11.86±0.77 [1/mmol·sec]

EXAMPLE 12

(a) 1,3-(N,N'-Tetrabenzyl)diamino-2-hydroxypropane 2.7 g (30 mmol) of 1,3-diamino-2-hydroxypropane and 14.3 ml (120 mmol) of benzyl bromide are refluxed with 8.3 g of potassium carbonate in ethanol/H₂O (10:1) overnight; then the suspension is evaporated to dryness and taken up in water and toluene. The organic phase is dried over sodium sulfate and, after evaporation of the toluene under vacuum, the resulting oil is chromatographed on silica gel in ethyl acetate/hexane (1:10). Yield: 11.9 g (88%) of a colorless oil.

Analysis: C 82.63 H 7.60 N 6.22 (Calcd.) C 82.56 H 7.69 N 6.13 (Found)

(b) 1,3-(N,N'-Tetrabenzyl)diamino-2-(oxiranylmethoxy)propane 9.01 g (20 mmol) of 1,3-(N,N'-tetrabenzyl)diamino-2-hydroxypropane (Example 12a) is dissolved in dichloromethane and added to a cooled (0° C.) solution of 4.69 ml (60 mmol) of epichlorohydrin and 340 mg of tetrabutylammonium bisulfate in 50% strength sodium hydroxide solution and then the mixture is vigorously stirred overnight at 40° C. The two-phase mixture is poured on about 100 ml of water, repeatedly extracted with dichloromethane, and the combined organic phases are dried over MgSO₄. After evaporation of the solvent, an oil is obtained (9.83 g, 97%).

Analysis: C 80.60 H 7.56 N 5.53 (Calcd.) C 79.97 H 7.51 N 5.21 (Found)

(c) 6,6',6'',6''',6'''',6'''''-Hexa[Bis[1-(N,N-dibenzylamino)-2-(N,N-dibenzylaminomethyl)-5-hydroxy-3-oxahexyl]amino]-6,6',6'',6''',6'''',6'''''-hexadeoxy-α-cyclodextrin 12.58 g (10 mmol) of 6,6',6'',6''',6'''',6'''''-hexamino-6,6',6'',6''',6'''',6'''''-hexadeoxy-α-cyclo-dextrin hexahydrochloride [J. Boger, R. J. Corcoran and J.-M. Lehn, Helv. Chim. Acta 61:2190–2218 (1978)] is combined in aqueous dioxane at pH 10 (set with 1N sodium hydroxide solution) with 91.20 g (180 mmol, 1.5-fold excess) of the epoxide described in Example 12(b), and stirred overnight at 50° C. The mixture is evaporated to dryness and chromatographed on silica gel in dichloromethane/methanol (10:1). Yield: 40.1 g (57%) of a pale-yellow oil.

Analysis: C 75.67 H 7.47 N 5.96 (Calcd.) C 75.19 H 7.59 N 5.39 (Found)

(d) 6,6',6'',6''',6'''',6'''''-Hexa[bis(1-amino-2-aminomethyl-5-hydroxy-3-oxahexyl)amino]-6,6',6'',6''',6'''',6'''''-hexadeoxy-α-cyclodextrin 35.24 g (5 mmol) of the benzyl-blocked 24-amine described in preceding Example 12(c) is suspended in aqueous ethanol and hydrogenated in an autoclave at 50° C. by means of H₂/Pd (10 bar). The resultant solution is evaporated to dryness and the thus-obtained amine is reacted without further purification. Yield: 28.6 g (96%) of a pale-yellow oil. An analytical sample was chromatographed on silica gel in dioxane/water/concentrated ammonia (3:1:1) and showed the following analysis:

C 72.48 H 7.60 N 7.04 (Calcd.) C 72.19 H 7.48 N 6.79 (Found)

(e) Gd Complex of the Conjugate of $N^3$-(2,6-Dioxomorpholinoethyl)-$N^6$-(ethoxycarbonylmethyl)-3,6-diazaoctanedioic Acid with 6,6',6'',6''',6'''',6'''''-Hexa[bis(1-amino-2-aminomethyl-5-hydroxy-3-oxahexyl)amino]-6,6',6'',6''',6'''',6'''''-hexadeoxy-α-cyclodextrin 2.98 g (0.5 mmol) of the 24-amine disclosed in Example 7(d) is dissolved in 150 ml of water. Then, within 2 hours, 14.52 g (36 mmol) of $N^3$-(2,6-dioxomorpholinoethyl)-$N^6$-(ethoxycarbonylmethyl)-3,6-diazaoctanedioic acid (Example 13a of EP 0,331,616) is added in portions in the solid form, the pH being maintained at 9.5 by adding 1N NaOH. Subsequently, the ethyl ester is saponified by adding 25 ml of 32% strength sodium hydroxide solution within 2 hours, set at pH 7 with "Amberlite" IR 120 (H⁺ form), and the ion exchanger is suctioned off. The solution is subjected to ultra-filtration ("AMICON" YM5) and freeze-dried. An analytical sample shows that 100 mg of polymeric complexing compound absorb 24.2 mg of Gd (indicator: xylenol orange). The lyophilized product (8.40 g) is dissolved in 400 ml of water and combined with 2.3 g of $Gd_2O_3$ ($\hat{=}$2.0 g Gd), stirred for 30 minutes at 80° C., set at neutral with ion exchanger, filtered, and freeze-dried.

Yield: 10.2 g of a colorless powder.
H₂O content (Karl-Fischer): 4.8%
Gd analysis (AAS): 17.0%
Melting point: >250° C. (decomposition)
T₁ relaxation (H₂O): 12.89±0.41 [1/mmol·sec](plasma): 13.17±0.32 [1/mmol·sec]

EXAMPLE 13

(a) 10-(2,6,7-Trihydroxy-4-oxaheptyl)-1,4,7-triscarboxymethyl-1,4,7,10-tetraazacyclododecane 19.56 g (103.92 mmol) of 2,2-dimethyl-4-(2',3'-epoxy)propoxymethyl-1,3-dioxolane and 10 g (28.86 mmol) of 1,4,7-triscarboxymethyl-1,4,7,10-tetraazacyclododecane (=DO3A) are dissolved in a mixture of 50 ml of dioxane/80 ml of water, and the pH value is set at 10 with 6N potassium hydroxide solution. The mixture is stirred for 24 hours at 70° C., then evaporated to dryness, the residue is taken up in 200 ml of water/50 ml of methanol, and extracted twice with 100 ml of tert-butylmethyl ether. The aqueous solution is adjusted to pH 3 with 5N hydrochloric acid and evaporated to dryness. The residue is decocted (extracted) with 200 ml of methanol/80 ml of dichloromethane. The mixture is cooled in an ice bath and filtered off from the precipitated potassium chloride. The filtrate is evaporated under vacuum, the residue is dissolved in 45 ml of water/20 ml of ethanol, and then passed over a column of poly(4-vinylpyridine). The product is eluted with a solution of ethanol/water 1:3. After evaporation under vacuum, the residue is chromatographed on a reversed phase column (RP 18/mobile phase=gradient of water/tetrahydrofuran). After evaporation of the main fraction, 10.13 g (71% of theory) of a strongly hygroscopic, vitreous solid is obtained.

Analysis (based on anhydrous substance): C 48.57 H 7.74 N 11.33 (Calcd.) C 48.46 H 7.81 N 11.24 (Found)

(b) Gd Complex of 10-(2,6,7-Trihydroxy-4-oxaheptyl)-1,4,7-triscarboxymethyl-1,4,7,10-tetraazacyclododecane 8.56 g (17.3 mmol) of the title compound of Example 13(a) is dissolved in 50 ml of deionized water, and 3.13 g (8.65 mmol) of gadolinium oxide is added. The mixture is heated to 90° C. for 3 hours. The cooled solution is stirred for one hour with 3 ml of an acidic ion exchanger (AMB 252c) and 3 ml of a weakly alkaline ion exchanger (IRA 67). The product is filtered off from the exchanger, and the filtrate is freeze-dried. Yield: 11.0 g (98% of theory) of a colorless amorphous powder.

Analysis (based on anhydrous substance): C 37.03 H 5.44 N 8.64 Gd 24.24 (Calcd.) C 37.00 H 5.51 N 8.57 Gd 24.18 (Found)

(c) Gd Complex of the N-(5-Hydroxy-3-oxahexyl-DO3A)-48-amino Cascade Polymer 38.93 g (60 mmol) of the Gd complex of Example 13(b) is dissolved in 400 ml of methanol, combined with 25.67 g (120 mmol) of $NaIO_4$ and stirred for 4 hours under exclusion of light. The product is then filtered off from the undissolved substance, and the filtrate is freeze-dried. The lyophilized product is dissolved with 6.52 g (0.625 mmol=30 mmol $NH_2$) of the 48-cascade amine described in Example 7(b) in 750 ml of buffer, pH 9.0 (Riedel de Haën, borax/HCl), and, after adding 11.32 g (180 mmol) of sodium cyanoborohydride, stirred at room temperature for 6 days. The solution is then desalted via an "AMICON" ultrafiltration membrane YM5 and finally freeze-dried.
Yield: 16.45 g (61% of theory)
$H_2O$ content (Karl-Fischer): 9.8%
Gd determination (AAS): 15.75%
$T_1$ relaxation ($H_2O$): 12.35+0.14 [1/mmol·sec](plasma): 14.74+0.33 [1/mmol·sec]

EXAMPLE 14

Gd Complex of the N-(2-Carboxyethyl)-N-(5-hydroxy-3-oxahexyl-DO3A)-48-amino Cascade Polymer 2.2 g of the polymer described in Example 13(c) with secondary amine in the linkages between complex and backbone is dissolved in 25 ml of methanol and added dropwise to a mixture of 20 ml (220 mmol) of methyl acrylate and 20 ml of methanol, and stirred for 3 days at room temperature. The solution is evaporated under vacuum, the pale-yellow oil is dissolved in 20 ml of 1N NaOH and saponified for 3 hours at room temperature. Then the product is neutralized with dilute HCl, and the solution is desalted via an "AMICON" ultrafiltration membrane YM5 and finally freeze-dried.
Yield: 2.20 g
$H_2O$ content (Karl-Fischer): 7.7%
Gd analysis (AAS): 14.93%
$T_1$ relaxation ($H_2O$): 11.47±0.14 [1/mmol·sec](plasma): 13.38±0.07 [1/mmol·sec]

Paper electrophoresis of the polymer at pH 9.0 (0.05-molar borax) and 10 V/cm shows migration toward the anode whereas the starting compound (Example 13c) migrates to the cathode under the same conditions.

EXAMPLE 15

Gd Complex of the N-(1,2-Dicarboxyethyl)-N-(5-hydroxy-3-oxahexyl-DO3A)-48-amino Cascade Polymer Under ice cooling, 23 ml of triethylamine is added dropwise to 14.3 g (110 mmol) of maleic acid monomethyl ester (Tokyo Chemical Industry Co. Ltd.) in 15 ml of methanol. The mixture is allowed to reach room temperature, 2.20 g of the polymer described in Example 13(c) in 25 ml of methanol is added dropwise to this solution, and the mixture is agitated for 3 days at room temperature. Then the mixture is combined with diethyl ether, decanted from the separated oil, the remaining residue is dissolved in 20 ml of 1N NaOH and saponified for 3 hours at room temperature. Then the mixture is neutralized with dilute HCl and the solution is desalted via an "AMICON" ultrafiltration membrane YM5 and finally freeze-dried.
Yield: 2.13 g
$H_2O$ content (Karl-Fischer): 7.9%
Gd analysis (AAS): 14.53%
$T_1$ relaxation ($H_2O$): 11.93±0.27 [1/mmol·sec](plasma): 13.27±0.09 [1/mmol·sec]

EXAMPLE 16

Gd Complex of the N-(Carboxymethyl)-N-(5-hydroxy-3-oxahexyl-DO3A)-48-amino Cascade Polymer 2.20 g of the polymer disclosed in Example 13(c) is dissolved in 25 ml of $H_2O$ and set at pH 10 by adding 1N NaOH. A solution of 2.6 g (22 mmol) of sodium chloroacetate in 20 ml of $H_2O$ is added slowly dropwise at 50° C. to this solution, and the pH is maintained at 10 by addition of 1N NaOH. After the addition step is completed, the mixture is stirred overnight at this temperature, then neutralized with dilute hydrochloric acid, and the solution is desalted via an "AMICON" ultrafiltration membrane YM5. After freeze-drying, 2.3 g of a flaky pwoder is obtained.
$H_2O$ content (Karl-Fischer): 10.5%
Gd analysis (AAS): 15.12%
$T_1$ relaxation ($H_2O$): 12.25±0.37 [1/mmol·sec](plasma): 12.93±0.14 [1/mmol·sec]

EXAMPLE 17

Gd Complex of the N-(Carboxymethoxyacetyl)-N-(5-hydroxy-3-oxahexyl-DO3A)-48-amino Cascade Polymer 2.20 g of the polymer described in Example 13(c) is dissolved in 25 ml of $H_2O$ and set to pH 9 by adding 1N NaOH. Under agitation, 850 mg (6.6 mmol) of diglycolic acid anhydride (Fluka) is added to this solution in portions, the pH being maintained at 9 by adding 2N NaOH. After the addition step is completed, the mixture is stirred for 15 minutes, neutralized with dilute hydrochloric acid, subjected to ultrafiltration ("AMICON" YM5), and finally freeze-dried.
Yield: 2.43 g
$H_2O$ content (Karl-Fischer): 8.3%
Gd analysis (AAS): 14.82%
$T_1$ relaxation ($H_2O$): 11.45±0.23 [1/mmol·sec](plasma): 13.74±0.20 [1/mmol·sec]

EXAMPLE 18

Thioureido Conjugate of the Gd Complex of 10-(6-Isothiocyanato-2-hydroxy-4-oxahexyl)-1,4,7-triscarboxymethyl-1,4,7,10-tetraazacyclododecane with the Gd Complex of the N-(5-Hydroxy-3-oxahexyl-DO3A)-48-amino Cascade Polymer 2.20 g of the polymer described in Example 13(c) is dissolved in 25 ml of $H_2O$. Under nitrogen, 3.09 g (4.7 mmol) of the isothiocyanate-Gd complex disclosed in Example 2(e) is added in portions in the solid form to this solution, and the mixture is stirred overnight at room temperature. After ultra-filtration ("AMICON" YM-10 membrane), the conductivity of the solution is set at a minimum by means of an ion exchanger ("Amberlite" IR 120, H⁺ form and IRA 410, OH⁻ form). The product is filtered off from the exchanger and freeze-dried.
Yield: 3.31 g
$H_2O$ content (Karl-Fischer): 7.3%
Gd analysis (AAS): 15.32%
$T_1$ relaxation ($H_2O$): 12.79+0.30 [1/mmol·sec](plasma): 14.21+0.05 [1/mmol·sec]

EXAMPLE 19

(a) 10-(2,3,4-Trihydroxybutyl)-1,4,7-triscarboxymethyl-1,4,7,10-tetraazacyclododecane 10.0 g (28.87 mmol) of 1,4,7-triscarboxymethyl-1,4,7,10-tetraazacyclododecane (DO3A) is dissolved in 40 ml of water, and the pH is set at 13 with 5N sodium hydroxide solution. A solution of 6.24 g (43.30 mmol) of 2-(2,2-dimethyl-1,3-dioxolan-4-yl)ethylene oxide (DE 3,150,917) in 10 ml of dioxane is added thereto, and the mixture is stirred for 24 hours at room temperature. The mixture is diluted with 60 ml of water and extracted three times with 50 ml of ether. The aqueous phase is brought to pH 2 with 10% strength hydrochloric acid and evaporated. The residue is dissolved in a small amount of water and passed to a cation exchange column (IR 120). After flushing with water, the ligand is eluted with 0.5-normal aqueous ammonia solution. The fractions are evaporated, the ammonium salt is taken up in a small amount of water and passed over an anion exchange column (IRA 67). The mixture is first washed with water and then eluted with 0.5-normal aqueous formic acid. The product is evaporated under vacuum, the residue is dissolved in a small amount of hot methanol, and acetone is added, thus crystallizing the title compound.
Yield: 11.31 g (87% of theory) of a white hygroscopic powder. $H_2O$ content (Karl-Fischer): 11.1%

Analysis (based on anhydrous substance): C 47.99 H 7.61 N 12.44 (Calcd.) C 47.93 H 7.67 N 12.40 (Found)

(b) Gadolinium Complex of 10-(2,3,4-Trihydroxybutyl)-1,4,7-triscarboxymethyl-1,4,7,10-tetraazacyclo-dodecane 10.0 g (22.2 mmol) of the compound obtained according to Example 19(a) is dissolved in 60 ml of deionized water, and 4.02 g (11.1 mmol) of gadolinium oxide is added. The mixture is heated for 3 hours to 90° C. The cooled solution is stirred with respectively 2 ml of acidic ion exchanger (IR 120) and 2 ml of alkaline exchanger (IRA 410) for one hour at room temperature, filtered off from the exchanger, and the filtrate is briefly boiled with active carbon. After filtration and freeze-drying, a white, amorphous powder is obtained.
Yield: 12.76 g (95% of theory).
$H_2O$ content (Karl-Fischer): 12.3%

Analysis (based on anhydrous substance): C 35.73 H 5.17 Gd 25.99 N 9.26 (Calcd.) C 35.68 H 5.24 Gd 25.93 N 9.21 (Found)

(c) Gd Complex of the N-(2-Hydroxypropyl-DO3A)-48-amino Cascade Polymer 13.8 g (20 mmol) of the Gd complex of Example 19(b) is dissolved in 120 ml of methanol, combined with 8.56 g (40 mmol) of $NaIO_4$, and stirred for 4 hours under exclusion of light. Then the mixtrure is filtered off from the undissolved matter, and the filtrate is freeze-dried. The lyophilized product is dissolved with 2.17 g (0.208 mmol=10 mmol —$NH_2$) of the 48-cascade amine described in Example 7(b) in 250 ml of buffer, pH 9.0 (Riedel de Haën, borax/HCl), and, after addition of 3.77 g (60 mmol) of sodium cyanoborohydride, stirred for 6 days at room temperature. The solution is then desalted via an "AMICON" ultrafiltration membrane YM5 and finally freeze-dried.
Yield: 5.87 g
$H_2O$ content (Karl-Fischer): 8.9%
Gd analysis (AAS): 15.93%
$T_1$ relaxation ($H_2O$): 13.22±0.23 [1/mmol·sec](plasma): 14.39±0.12 [1/mmol·sec]

EXAMPLE 20

Gd Complex of the N-(carboxymethoxyacetyl)-N-(2-hydroxy-propyl-DO3A)-48-amino Cascade Polymer 1.7 g of the polymer described in Example 19(c) is dissolved in 20 ml of $H_2O$ and set to pH 9 by addition of 1N NaOH. Under agitation, 772 mg (6 mmol) of diglycolic acid anhydride (Fluka) is added thereto in portions, the pH being maintained at 9 by addition of 2N NaOH. After the addition is finished, the mixture is further stirred for 15 minutes, neutralized with dilute hydrochloric acid, subjected to ultrafiltration ("AMICON" YM5), and finally freeze-dried.
Yield: 1.90 g
$H_2O$ content (Karl-Fischer): 10.7%
Gd analysis (AAS): 14.93%
$T_1$ relaxation ($H_2O$): 13.52±0.22 [1/mmol·sec](plasma): 15.01±0.37 [1/mmol·sec]

EXAMPLE 21

Conjugate of the Gd Complex of 10-(9-Bromo-2-hydroxy-8-oxo-4-oxa-7-azanonyl)-1,4,7-triscarboxymethyl-1,4,7,10-tetraazacyclododecane with the Gd Complex of the N-(5-Hydroxy-3-oxahexyl-DO3A)-48-amino Cascade Polymer 1.7 g of the polymer disclosed in Example 19(c) is dissolved in 20 ml of $H_2O$ and set to pH 9.5 by addition of 2N NaOH. At 40° C., 4.43 g (6 mmol) of the Gd complex described in Example 3 is added thereto under agitation, the pH being maintained at 9.5 by adding 2N NaOH. After 24 hours at 40° C., the mixture is neutralized with dilute hydrochloric acid, subjected to ultrafiltration ("AMICON" YM5), and finally freeze-dried.
Yield: 2.45 g
$H_2O$ content (Karl-Fischer): 9.7%
Gd analysis (AAS): 15.72%
$T_1$ relaxation ($H_2O$): 13.07+0.23 [1/mmol·sec](plasma): 14.39+0.15 [1/mmol·sec]

EXAMPLE 22

Yttrium-90 Complex of the [10-Carboxy-3,6,9-tris-(carboxymethyl)-3,6,9-triazadecanoyl] Derivative of the 48-Amine of the Tris(aminoethyl)amine Cascade Polymer 1.04 g (35 µmol) of the 48-DTPA-ethyl ester described in Example 7(c) is dissolved, as described in Example 8, in 10 ml of NaOH, stirred for 4 hours at room temperature, and set to pH 7 with "Amberlite" IR 120 (H⁺ form). The mixture is suctioned off from the ion exchanger and the solution is freeze-dried, thus obtaining 0.98 g. Of this amount, 9.8 mg is added to yttrium-90 (yttrium chloride, Amersham; 11 µCi) in 100 µl of 0.1-molar tetramethylammonium acetate, pH 5. After 10 minutes, control by thin-layer chromatography reveals that complexing has taken place completely. The mixture is subsequently dialyzed via a "Centricoh" 10 ultrafiltration unit (Amersham).

Example for in vivo NMR Diagnostics

The test animals (rats, Wistar Hah ♂) are anesthetized for the nuclear spin tomograph examination ("Rompun"+ "Ketavet") and are provided with a catheter in the caudal vein for administration of the contrast medium. The test is performed in an MRI experimental device by General Electric (field strength 2 tesla). The images are produced with a saturation inversion projection (SIP) sequence. This is a standard saturation and inversion recovery pulse sequence wherein the signals of all tissues except for the blood are suppressed. Prior to utilization of the contrast medium, the sequence is optimized to minimum intensity [typical values: T (saturation)=50–60 msec; T (inversion)=40–50 msec].

Figure 1:
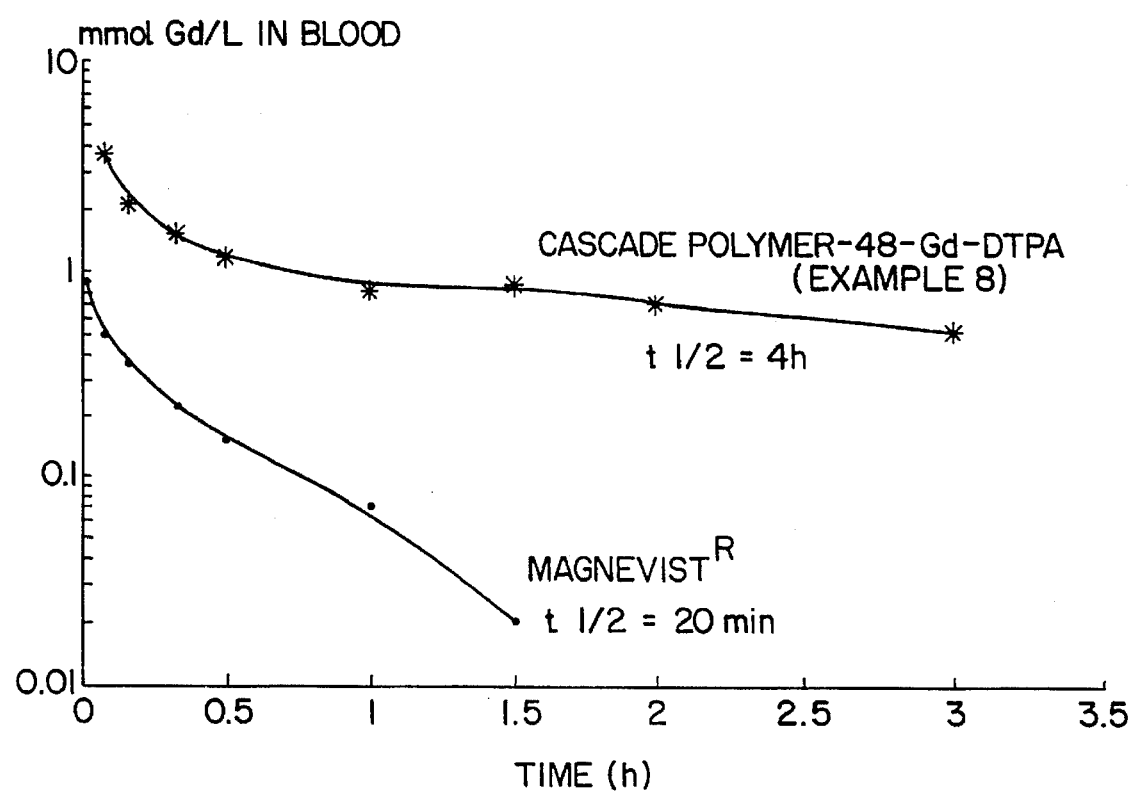
FIG. 1: Concentration-time curve of the cascade polymer described in Example 8 as compared with "Magnevist" after intravenous administration of 0.2 mmol/kg in rats. In spite of an identical dose, a marked difference is observed in the concentration of the two contrast media in the blood: "Magnevist" is distributed in the extracellular space whereas the cascade polymer is distributed only in the vasal space and consequently reaches markedly higher concentrations.
Figure 2:
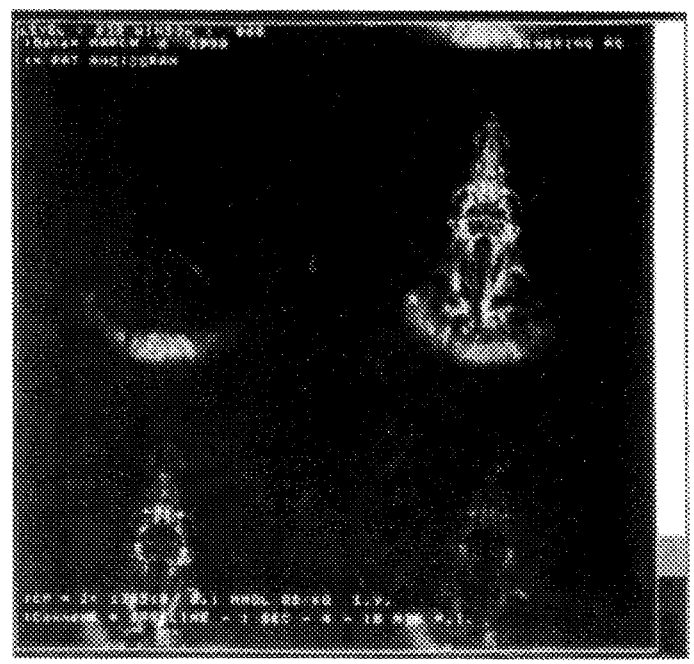
FIG. 2: Coronary projection image of head-neck region of a rat.

FIG. 2 shows the angiographic visualization of the head-neck region of a rat. The scan without contrast medium (top left-hand side) shows almost no signal at all. (Imaging period for all scans is 1 minute.) After administration of the title compound of Example 8 (0.1 mmol Gd/kg), an excellent contrasting of the vessels results, becoming weaker with time in correspondence with the elimination of the compound (1b=1 second, 1c=4 minutes, and 1d=10 minutes p.i.).

FIG. 3 shows an angiographic scan of the abdominal zone of a rat (Lew Mol O) produced after a dose of 0.25 mmol Gd/kg under otherwise identical conditions as in the preceding example. The animal carries a tumor at the left thigh (on the right-hand side as seen by the observer). The vessel structures, altered in this area, and/or the vessels feeding the tumor, as well as many other relevant vessels of the abdominal zone, are excellently contrasted.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a method of NMR imaging of a patient comprising administering to the patient an effective amount of a contrast agent and NMR imaging the patient, the improvement wherein the contrast agent comprises a cascade polymer, being a chelate with at least five ions of an element of atomic numbers 21–29, 42, 44 or 58–70, complexed with an agent of Formula I

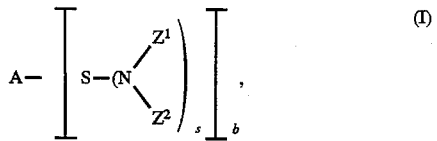

wherein

A is a nitrogen-containing cascade nucleus of basis multiplicity b of the formula:

$NR^2R^3R^4$,

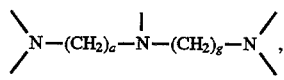

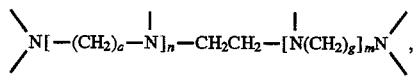

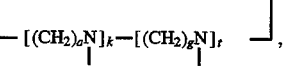

wherein $R^2$, $R^3$ and $R^4$ are, in each case independently of one another, a covalent bond or $-(CH_2)_k-(C_6H_4)_r-(CH_2)_l-N<$, g is the number 2, 3, 4 or 5, t is the number 1, 2, 3, 4, 5, 6, 7 or 8, l is the number 0, 1, 2, 3, 4 or 5, r is the number 0 or 1 n is the number 0 1 2 3 or 4 m is the number 0, 1, 2, 3 or 4, k is the number 1, 2, 3, 4 or 5, a is the number 2, 3, 4 or 5, W is CH, $CH_2$, NH or a nitrogen atom, $C_1$ is $(CH_2)_k-N<$, $C_2$, $C_3$, $C_4$ and $C_5$ are, in each case independently, a hydrogen atom or $(CH_2)_f-N<$, f is the number 1, 2, 3, 4 or 5, j is the number 6, 7 or 8, $Y^1$ and $Y^2$ are, in each case independently of each other, a hydrogen atom, $CH_2-CH(OH)-CH_2N<$ or $(CH_2)_a-N<$, and $Y_3$ is a nitrogen atom, $O-CH_2-CH(OH)-CH_2N<$ or $O-(CH_2)_g-N<$, a and g are as defined above, $\doteq$ means a single or double bond, with the proviso that, if $Y^3$ is a nitrogen atom, $Y^1$ and $Y^2$ are hydrogen;

S is a repeating unit of the formula:

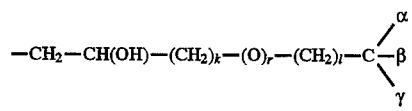

α and β each independently is a hydrogen atom or $(CH_2)_o$,

γ means $(CH_2)_p$ each f independently is the number 1, 2, 3, 4 or 5, and r is the number 0 or 1, and k is 1, 2, 3, 4 or 5, l is 0, 1, 2, 3, 4 or 5, l is 0, 1, 2, 3, 4 or 5, o is 0, 1, 2, 3, 4 or 5, with the proviso that l and o are not both zero at the same time;

N is a nitrogen atom, $Z^1$ and $Z^2$, for the first to penultimate generation, in each case are

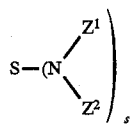

and, for the last generation, $Z^1$ is hydrogen, a $C_1$–$C_{10}$-alkyl, $C_2$–$C_{10}$-carboxylic acyl or $C_1$–$C_{10}$-alkylsulfonyl, each optionally containing 1–3 carboxy, 1–3 sulfonic acid, 1–5 hydroxy groups and/or 1–3 oxa atoms, or is the residue of a chelating agent or chelate K, and $Z^2$ is, to an extent of 96–100% of the total $Z^2$ content, the residue of an attached chelating agent or chelate K and, to an extent of 4–0%, V', wherein V' is V having at its end a functional group or, linked via this functional group, which is: —NH$_2$; —NHR; —NHNH$_2$; NRNH$_2$; SH; OH; —COCH$_3$; CH=CH—CO$_2$R; —NCS; NCO;

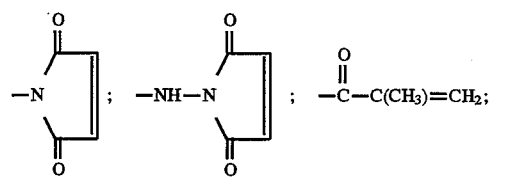

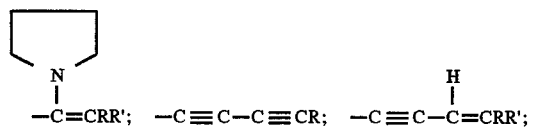

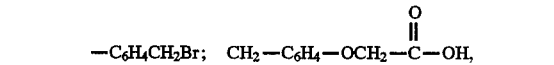

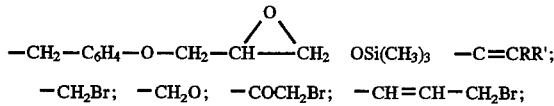

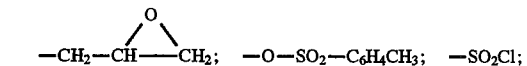

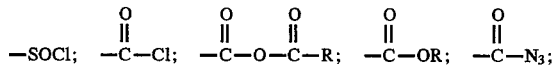

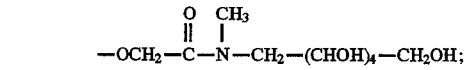

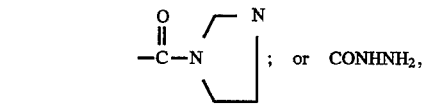

wherein R and R' are identical or different and in each case are hydrogen, a saturated or unsaturated $C_1$–$C_{20}$-hydrocarbyl residue optionally substituted by a phenyl group, or a phenyl group, or, linked via this function group, a bio- or macromolecule, V being a straight-chain, $C_1$–$C_{20}$-alkylene group which optionally contains imino, phenylene, phenylenoxy, phenylenimino, amide, hydrazide, ureido, thioureido, carbonyl and/or ester group(s) and/or oxa, sulfur and/or nitrogen atom(s), and is optionally substituted by carboxyl, carboxylalkyl, hydroxy, mercapto, imino, epoxy, oxo, thioxo, and/or amino, b is a number 1 through 50, and s is a number 1 to 3, wherein the reproduction units S need be identical only for a given generation, and the residue of the chelating agent or chelate K is a residue of Formulae I A, I B or I C:

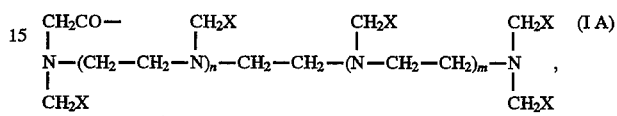

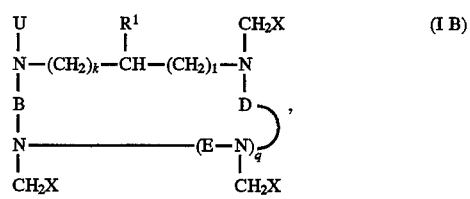

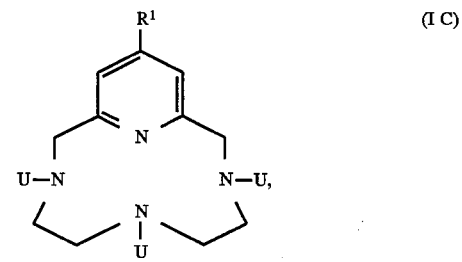

bound to the terminal nitrogen atoms of the final generation by a —CH$_2$CO— or V group, n and m in each case independently is 0, 1, 2, 3 or 4, n and m adding up to no more than 4, k is the number 1, 2, 3, 4 or 5, l is the number 0, 1, 2, 3, 4 or 5, q is the number 0, 1 or 2, U is CH$_2$X or V, X is in each case independently —COOH or V' wherein, if the molecule contains V', at least 0.1% of the substituents X stand for V', B, D and E, being identical or different, are in each case —(CH$_2$)$_a$ with a being the number 2, 3, 4 or 5, $R^1$ is V or a hydrogen atom, with the proviso that $R^1$ is V only if U is CH$_2$X at the same time, and that U is V only if $R^1$ is a hydrogen atom at the same time, and wherein optionally, a portion of the COOH groups are present in the form of a corresponding ester of a $C_1$–$C_6$-alkyl group or amide of a saturated or unsaturated, linear, branched or cyclic hydrocarbon of 1–5 carbon atoms, optionally substituted with 1 to 3 hydroxy or $C_1$–$C_4$-alkoxy or a 5- or 6-membered ring including the amide nitrogen;

or a salt thereof with a cation of an inorganic and/or organic base, an amino acid or an amino acid amide.

2. The method of claim 1, wherein the bio- or macromolecule(s) optionally contained in V' is/are an antibody or antibodies or antibody fragment or fragments.

3. The method of claim 1, wherein the bio- or macromolecule(s) optionally contained in V' is/are a protein or proteins.

4. The method of claim 3, Wherein the protein albumin, globulin or lectin.

5. The method of claim 1, wherein the bio- or macromolecule(s) optionally contained in V' is/are a polysaccharide or polysaccharides.

6. The method of claim 5, wherein the polysaccharide is starch, dextran or dextrin.

7. The method of claim 1, wherein V is

—CH$_2$—CH(OH)—CH$_2$—O—CH$_2$CH$_2$—;
—CH$_2$—CH(OH)—CH$_2$—;

—CH$_2$—CH(OH)CH$_2$O—CH—CO—;
　　　　　　　　　　　|
　　　　　　　　　　CH$_2$COOH

—CH$_2$—CH(OH)—CH$_2$—O—CH—CH$_2$CO—;
　　　　　　　　　　　　|
　　　　　　　　　　　CH$_2$COOH

—CH$_2$—CH(OH)—CH$_2$—O—CH$_2$CH$_2$—N—CH$_2$CO—;
　　　　　　　　　　　　　　　　|
　　　　　　　　　　　　　　　CH$_2$COOH

—CH$_2$—CH(OH)—CH$_2$—O—CH$_2$CH—CH$_2$CO—;
　　　　　　　　　　　　　|
　　　　　　　　　　　　COOH

—CH$_2$—CH(OH)—CH$_2$—O—CH$_2$—CH—CH$_2$CO—;
　　　　　　　　　　　　　　|
　　　　　　　　　　　　CH$_2$—COOH

—CH$_2$CH(OH)—CH$_2$O—CH$_2$CH$_2$—O—CH$_2$CH$_2$—N—CH$_2$CO—;
　　　　　　　　　　　　　　　　　　　|
　　　　　　　　　　　　　　　　　CH$_2$COOH

—CH$_2$—CH(OH)—CH$_2$—OCH$_2$—C$_6$H$_4$—NH—CO—CH$_2$—;
—CH$_2$—CH(OH)—CH$_2$—OCH$_2$—C$_6$H$_4$—NH—CO—CH$_2$—S—(CH$_2$)$_4$—S—;

—CH$_2$—CH(OH)—CH$_2$—OCH$_2$—C$_6$H$_4$—NH—CO—CH$_2$—NH—C(=O)—CH(R$^4$)—NH—C(=O)—CH(R$^y$)—NH—C(=O)—CH$_2$—.

wherein R$^+$ and R$^y$ stand for natural amino acid residues;

—CH$_2$—CH(OH)—CH$_2$—O—(CH$_2$)$_2$—NHCS—;
—CH$_2$—CH(OH)—CH$_2$—NHCS—; —CH$_2$—CH(OH)—CH$_2$—O—(CH$_2$)$_2$—O—(CH$_2$)$_2$NHCS—;
—CH$_2$—CH(OH)—CH$_2$—O—(CH$_2$)$_2$—NH—CO—CH$_2$—; —CH$_2$—CH(OH)—CH$_2$—O—C$_6$H$_4$—NHCS—; —CH$_2$—CH(OH)—CH$_2$—O—C$_6$H$_4$—NHCO—; —CH$_2$—CH(OH)—CH$_2$—O—CH$_2$C$_6$H$_4$—NHCS—; —CH$_2$—O—C$_6$H$_4$—CH$_2$—; —CH$_2$—CH(OH)—CH$_2$—O—C$_6$H$_4$—CH$_2$—; —C(=NH)—O—C$_6$H$_4$—CH$_2$—; —(CH$_2$)$_4$—NH—CO—CH$_2$—O—C$_6$H$_4$—CH$_2$—; —(CH$_2$)$_4$—NH—CH$_2$—CH(OH)—CH$_2$—O—C$_6$H$_4$—CH$_2$—; —(CH$_2$)$_3$—O—C$_6$H$_4$—CH$_2$—; —CH$_2$—CO—NH—(CH$_2$)$_3$—O—CH$_2$—; —CH$_2$—CO—NH—NH—; —CH$_2$—CONH—(CH$_2$)$_2$—; —CH$_2$—CO—NH—(CH$_2$)$_{10}$—; —CH$_2$—CONH—(CH$_2$)$_2$—S—; —(CH$_2$)$_4$—NH—CO—(CH$_2$)$_8$—; —CH$_2$—CO—NH—(CH$_2$)$_3$—NH—; or —(CH$_2$)$_3$—NH—.

8. The method of claim 1, wherein the cascade polymer has 2–6 generations of reproduction units.

9. The method of claim 1, wherein, in the contrast agent, S for each generation is independently selected from one of the following:

—CH$_2$—CH(OH)—CH$_2$—;
—CH$_2$—CH(OH)—CH$_2$—O—(CH$_2$)$_2$—;

-continued

—CH$_2$—CH(OH)—CH$_2$—O—CH(CH$_2$—)(CH$_2$—) ;

—CH$_2$—CH(OH)—CH$_2$—O—CH$_2$—CH(CH$_2$—)(CH$_2$—) ;

—CH$_2$—CH(OH)—CH$_2$—O—CH$_2$—C(CH$_2$—)(CH$_2$—)(CH$_2$—).

10. The method of claim 1, wherein the at least five ions are selected from gadolinium (III), terbium (III), dyprosium (III), holmium (III), erbium (III) and iron (III).

11. The method of claim 1, wherein the contrast agent is administered as a solution containing 1 μmol/l to 1 mol/l of the contrast agent.

12. The method of claim 1, wherein the contrast agent is administered in an amount of 0.0001–5 mmol/kg of the patient.

13. The method of claim 1, wherein in formula (I), A and the corresponding b are as follows:
tris(aminoethyl)amine (b=6);
tris(aminopropyl)amine (b=6);
diethylenetriamine (b=5);
triethylenetetramine (b=6);
tetraethylenepentamine (b=7);
H$_2$N—CH$_2$—C$_6$H$_4$—CH$_2$—NH—CH$_2$—C$_6$H$_4$—NH$_2$ (b=5);

1,3,5-tris(aminomethyl)benzene (b=6);
2,4,6-tris(aminomethyl)pyridine (b=6);
1,4,7-triazacyclononane (b=3);
1,4,7,10-tetraazacyclododecane (b=4);
1,4,7,10,13-pentaazacyclopentadecane (b=5);
1,4,8,11-tetraazacyclotetradecane (b=4);
1,4,7,10,13,16,19,22,25,28-decaazacyclotriacontane (b=10);
6,6',6'',6''',6'''',6'''''-hexaamino-6,6',6'',6'''-6'''',6'''''-hexadeoxy-α-cyclodextrin (b=12);
6,6',6'',6''',6'''',6''''',6''''''-heptaamino-6,6',6'',6''',6'''',6''''', 6''''''-heptadeoxy-β-cyclodextrin (b=14);
6,6',6'',6''',6'''',6'''''-hexa-(1-amino-2-hydroxy-propyl)-α-cyclodextrin hexaether (b=12);
2,2',2'',2''',2'''',2''''',6,6',6'',6''',6'''',6'''''-dodeca-(1-amino-2-hydroxypropyl)-α-cyclodextrin dodecaether (b=24).

14. The method of claim 1, wherein K in formula (I) is: ethylenediaminetetraacetic acid, diethylenetriaminepentaacetic acid, trans-1,2-cyclohexanediaminetetra-acetic acid, 1,4,7,10-tetraazacyclododecanetetraacetic acid, 1,4,7-triazacyclononanetriacetic acid, 1,4,8,11-tetraazatetradecanetetraacetic acid, 1,5,9-triazacyclododecanetriacetic acid, 1,4,7,10-tetraazacyclododecanetriacetic acid or 3,6,9,15-tetraazabicyclo[9.3.1]pentadeca-1(15),11,13-trienetriacetic acid.

* * * * *